US012753238B2

(12) United States Patent
Marambaud

(10) Patent No.: US 12,753,238 B2
(45) Date of Patent: Oct. 6, 2026

(54) AGONIST ANTIBODIES AGAINST ENDOGLIN AND USES THEREOF

(71) Applicant: The Feinstein Institutes for Medical Research, Manhasset, NY (US)

(72) Inventor: Philippe Marambaud, Astoria, NY (US)

(73) Assignee: The Feinstein Institutes for Medical Research, Manhasset, NY (US)

( * ) Notice: Subject to any disclaimer, the term of this patent is extended or adjusted under 35 U.S.C. 154(b) by 884 days.

(21) Appl. No.: 17/799,397

(22) PCT Filed: Feb. 17, 2021

(86) PCT No.: PCT/US2021/018332

§ 371 (c)(1),
(2) Date: Aug. 12, 2022

(87) PCT Pub. No.: WO2021/167952

PCT Pub. Date: Aug. 26, 2021

(65) Prior Publication Data

US 2023/0075244 A1 Mar. 9, 2023

Related U.S. Application Data

(60) Provisional application No. 62/978,915, filed on Feb. 20, 2020.

(51) Int. Cl.

*C07K 16/28* (2006.01)
*A61P 35/00* (2006.01)
*A61K 39/00* (2006.01)

(52) U.S. Cl.

CPC .......... *C07K 16/2863* (2013.01); *A61P 35/00* (2018.01); *A61K 2039/505* (2013.01); *C07K 2317/52* (2013.01); *C07K 2317/622* (2013.01)

(58) Field of Classification Search

CPC ............ C07K 16/2863; C07K 2317/52; C07K 2317/622; C07K 2317/75; C07K 16/2896; A61P 35/00; A61K 2039/505

See application file for complete search history.

(56) References Cited

U.S. PATENT DOCUMENTS

| | | | |
|---|---|---|---|
| 2003/0185827 A1 | 10/2003 | Rodriguez et al. | |
| 2011/0256154 A1 | 10/2011 | Vincent et al. | |
| 2014/0037736 A1 | 2/2014 | Shi et al. | |
| 2014/0271629 A1 | 9/2014 | Corbit et al. | |
| 2016/0257755 A1 | 9/2016 | Theuer | |
| 2017/0000901 A1 * | 1/2017 | Stull | A61K 47/6865 |
| 2018/0146649 A1 | 5/2018 | Chuang | |
| 2018/0258156 A1 | 9/2018 | Grinberg et al. | |

FOREIGN PATENT DOCUMENTS

| | | | |
|---|---|---|---|
| WO | WO-9527045 A1 * | 10/1995 | C12N 9/0002 |
| WO | 2008054606 A2 | 5/2008 | |
| WO | 2010037835 A2 | 4/2010 | |
| WO | 2010145895 A1 | 12/2010 | |
| WO | 2015001085 A1 | 1/2015 | |
| WO | 2017100429 A1 | 6/2017 | |
| WO | 2018137705 A1 | 8/2018 | |
| WO | 2019228509 A1 | 12/2019 | |

OTHER PUBLICATIONS

Paul, WE, “Fundamental Immunology: Third Edition”, 1993, Raven Press, 292-295. (Year: 1993).*
Bendig, MM, “Humanization of Rodent Monoclonal Antibodies by CDR Grafting”, 1995, Methods: A Companion to Methods in Enzymology, 8, 83-93. (Year: 1995).*
Rudikoff, S et. al. “Single amino acid substitution altering antigen-binding specificity”, 1982, Proceedings of the National Academy of Sciences USA, 79, 1979-1983. (Year: 1982).*
Baxevanis, CN, “Antibody-based cancer therapy”, 2008, Expert Opin. Drug Discov., 3(4), 441-452. (Year: 2008).*
Wall, RJ, “Transgenic Livestock: Progress and Prospects for the Future”, 1996, Theriogenology, 45, 57-68. (Year: 1996).*
Houdebine, LM, “Production of pharmaceutical proteins by transgenic animals”, 2009, Comparative Immunology, Microbiology, and Infectious Diseases, 32, 107-121. (Year: 2009).*
Kappel, CA et. al. “Regulating gene expression in transgenic animals”, 1992, Current Opinion in Biotechnology, 3, 548-553. (Year: 1992).*
Evans, TRJ and Kaye, SB, “Vaccine therapy for cancer—fact or fiction?”, 1999, Q. J. Med., 92, 299-307. (Year: 1999).*
Komenaka, I et. a. “Immunotherapy for Melanoma”, 2004, Clinics in Dermatology, 22, 251-265. (Year: 2004).*
Hernandez-Ledesma, B et. al. “Lunasin, a novel seed peptide for cancer prevention”, 2009, Peptides, 30, 426-430. (Year: 2009).*
Schiffman, M and Castle, PE, “The Promise of Global Cervical-Cancer Prevention”, 2005, N. Engl. J. Med., 335(20), 2101-2104. (Year: 2005).*
Cuzick, J et. al. “Overview of the main outcomes in breast-cancer prevention trials”, 2003, Lancet, 361, 296-300. (Year: 2003).*
International Search Report and Written Opinion dated Aug. 12, 2021 issued in PCT International Application No. PCT/US2021/018332.
Kumar et al., “Antibody-Directed Coupling of Endoglin and MMP-14 is a Key Mechanism for Endoglin Shedding and Deregulation of TGF-β Signaling,” published online Sep. 30, 2013, Oncogene, 2014, vol. 33, pp. 3970-3979.

* cited by examiner

*Primary Examiner* — Laura B Goddard
*Assistant Examiner* — Alyssa Rae Stonebraker
(74) *Attorney, Agent, or Firm* — Amster, Rothstein & Ebenstein LLP

(57) ABSTRACT

Provided are agonist anti-ENG coreceptor-specific antibodies and agonist anti-ENG coreceptor-binding fragments thereof, including antibodies that bind to the BMP9-binding region within an ectodomain of an ENG coreceptor, as well as methods of use employing such antibodies and/or fragments in treating diseases such as HHT and PAH.

20 Claims, 3 Drawing Sheets

Specification includes a Sequence Listing.

AGONIST ANTIBODIES AGAINST ENDOGLIN AND USES THEREOF

CROSS-REFERENCE TO RELATED APPLICATIONS

This application is a U.S. national stage entry under 35 U.S.C. § 371 of PCT International Patent Application No. PCT/US2021/018332, filed Feb. 17, 2021, which claims benefit of U.S. Provisional Application No. 62/978,915, filed Feb. 20, 2020, the contents of which are hereby incorporated by reference.

BACKGROUND OF THE INVENTION

The disclosures of all publications, patents, patent application publications and books referred to herein, are hereby incorporated by reference in their entirety into the subject application to more fully describe the art to which the subject invention pertains.

Hereditary hemorrhagic telangiectasia (HHT) is an autosomal dominant genetic disorder characterized by the development of potentially life-threatening vascular anomalies in several organs in the form of arteriovenous malformations (AVMs). Particularly affected is the vasculature of the liver, lungs, and oronasal and gastrointestinal mucosa. In its most severe manifestations, HHT can lead to highly debilitating and life-threatening events, such as internal bleeding consecutive to the rupture of a hepatic or pulmonary AVM. HHT, and also familial pulmonary arterial hypertension (PAH), are caused by loss-of-function mutations in the endoglin signaling pathways.

New approaches to treating and preventing HHT and PAH are desired.

SUMMARY OF THE INVENTION

An antibody or antigen-binding fragment thereof comprising a heavy chain comprising one or more of:

```
                              (SEQ ID NO: 3)
GFTFNTYA

                              (SEQ ID NO: 4)
IRSKSSNYAT

                              (SEQ ID NO: 5)
VRDRTGSWFAY;
```

and a light chain comprising one or more of:

```
                              (SEQ ID NO: 6)
QDIGSS
                              (SEQ ID NO: 7)
ATS
                              (SEQ ID NO: 8)
LQYASSPYT.
```

An agonist anti-ENG coreceptor antibody, or ENG coreceptor-binding fragment thereof, which comprises:

a heavy chain comprising each of the following CDRs:

```
                              (SEQ ID NO: 3)
GFTFNTYA
```

-continued

```
                              (SEQ ID NO: 4)
IRSKSSNYAT

                              (SEQ ID NO: 5)
VRDRTGSWFAY;
```

and a light chain comprising one or more of the following CDRs:

```
                              (SEQ ID NO: 6)
QDIGSS

                              (SEQ ID NO: 7)
ATS

                              (SEQ ID NO: 8)
LQYASSPYT.
```

An agonist anti-ENG coreceptor antibody or ENG coreceptor-binding fragment thereof which binds to a human endoglin coreceptor.

An antibody or antigen-binding fragment thereof which binds to and is agonistic at an endoglin coreceptor and comprises a heavy chain encoded by SEQ ID NO:10.

An antibody or antigen-binding fragment thereof which binds to and is agonistic at an endoglin coreceptor and comprises a heavy chain having SEQ ID NO:17.

An antibody or antigen-binding fragment thereof which binds to and is agonistic at an endoglin coreceptor and comprises a light chain encoded by SEQ ID NO:12.

An antibody or antigen-binding fragment thereof which binds to and is agonistic at an endoglin coreceptor and comprises a light chain having SEQ ID NO:18.

An ScFv encoded by the nucleotide sequence set forth in one of SEQ ID NOs:13, 14, 15 or 16. An ScFv comprising SEQ ID NO:17 and SEQ ID NO:18. An ScFv which is an agonist at an ENG coreceptor and comprises at least one of SEQ ID NO:17 and SEQ ID NO:18. An ScFv which is an agonist at an ENG coreceptor and comprises SEQ ID NOS:3-5 and 6-8.

An isolated agonist endoglin coreceptor antibody or antibody fragment that: specifically binds to the epitope set forth in SEQ ID NO:1 or SEQ ID NO:2, the antibody or antibody fragment comprising a heavy chain variable region comprising the CDR sequences set forth in SEQ ID NOs:3-5; and/or a light chain variable region comprising the CDR sequences set forth in SEQ ID NOs:6-8; or cross-competes for specific binding with a reference antibody to the epitope set forth in SEQ ID NO:1 or SEQ ID NO:2, the reference antibody comprising a heavy chain variable region comprising the CDR sequences set forth in SEQ ID NOs:3-5; and/or a light chain variable region comprising the CDR sequences set forth in SEQ ID NOs: 6-8.

A method of detecting an ENG coreceptor-positive cell in a subject or a sample comprising administering to the subject, or contacting the sample with, an amount of an antibody or ENG coreceptor binding fragment thereof as provided herein, having a detectable marker conjugated thereto, in an amount effective to label an ENG coreceptor-positive cell and then detecting the presence of and/or quantifying the level of the label in the subject, thereby detecting an ENG coreceptor-positive cell in the subject or the sample.

A pharmaceutical composition comprising an amount of an antibody or ENG coreceptor-binding fragment thereof as provided herein, and a pharmaceutically acceptable carrier or excipient.

A method of treating hereditary hemorrhagic telangiectasia or preventing one or more symptoms of hereditary hemorrhagic telangiectasia in a subject comprising administering to the subject an amount of an antibody or ENG coreceptor binding-fragment thereof as provided herein, or a composition comprising such, effective to treat or prevent one or more symptoms of hereditary hemorrhagic telangiectasia.

A method of treating pulmonary arterial hypertension or preventing one or more symptoms of pulmonary arterial hypertension in a subject comprising administering to the subject an amount of an antibody or ENG coreceptor binding-fragment thereof as provided herein, or a composition comprising such, effective to treat or prevent one or more symptoms of pulmonary arterial hypertension.

A method of activating activin receptor-like kinase 1 (ALK1) signaling or ALK1-ENG-BMPR2 receptor activation by an ENG co-receptor comprising contacting the ENG co-receptor with an amount of an antibody or ENG coreceptor binding fragment thereof as provided herein.

A method of effecting phosphorylation of at least one of endothelial SMAD1, SMAD5 and SMAD8 associated with activation of an ENG co-receptor comprising contacting the ENG co-receptor with an amount of an antibody or ENG coreceptor-binding fragment thereof as provided herein.

A method of treating a cancer in a subject comprising administering to the subject an amount of an antibody or ENG coreceptor-binding fragment thereof as provided herein, or a composition comprising such, effective to treat a cancer in a subject.

A method of activating a Notch signaling pathway in a subject comprising administering to the subject an amount of an antibody or ENG coreceptor binding fragment thereof, or a composition comprising such, effective to activate a Notch signaling pathway in a subject.

A nucleic acid encoding a heavy chain of an antibody or fragment thereof as described herein is provided. A nucleic acid encoding a light chain of an antibody or fragment thereof as described herein is provided.

A nucleic acid encoding a heavy chain of an antibody which comprises one or more of:

```
                    (SEQ ID NO: 3)
GFTFNTYA

                    (SEQ ID NO: 4)
IRSKSSNYAT

                    (SEQ ID NO: 5)
VRDRTGSWFAY.
```

A nucleic acid encoding a light chain of an antibody which comprises one or more of:

```
                    (SEQ ID NO: 6)
QDIGSS

                    (SEQ ID NO: 7)
ATS

                    (SEQ ID NO: 8)
LQYASSPYT.
```

Use of amount of an antibody or ENG coreceptor-binding fragment thereof as provided herein for the manufacture of a medicament for treating, or preventing a symptom of, hereditary hemorrhagic telangiectasia.

Use of amount of an antibody or ENG coreceptor-binding fragment thereof as provided herein for the manufacture of a medicament for treating or preventing pulmonary arterial hypertension.

Use of amount of an antibody or ENG coreceptor-binding fragment thereof as provided herein for the manufacture of a medicament for treating or preventing a squamous cell cancer.

A pharmaceutical composition comprising an effective amount of the isolated antibody or antibody fragment as described herein, and a pharmaceutically acceptable carrier or excipient, is provided.

BRIEF DESCRIPTION OF THE DRAWINGS

Those of skill in the art will understand that the drawings, described below, are for illustrative purposes only. The drawings are not intended to limit the scope of the present teachings in any way.

DETAILED DESCRIPTION OF THE INVENTION

Figure 1:
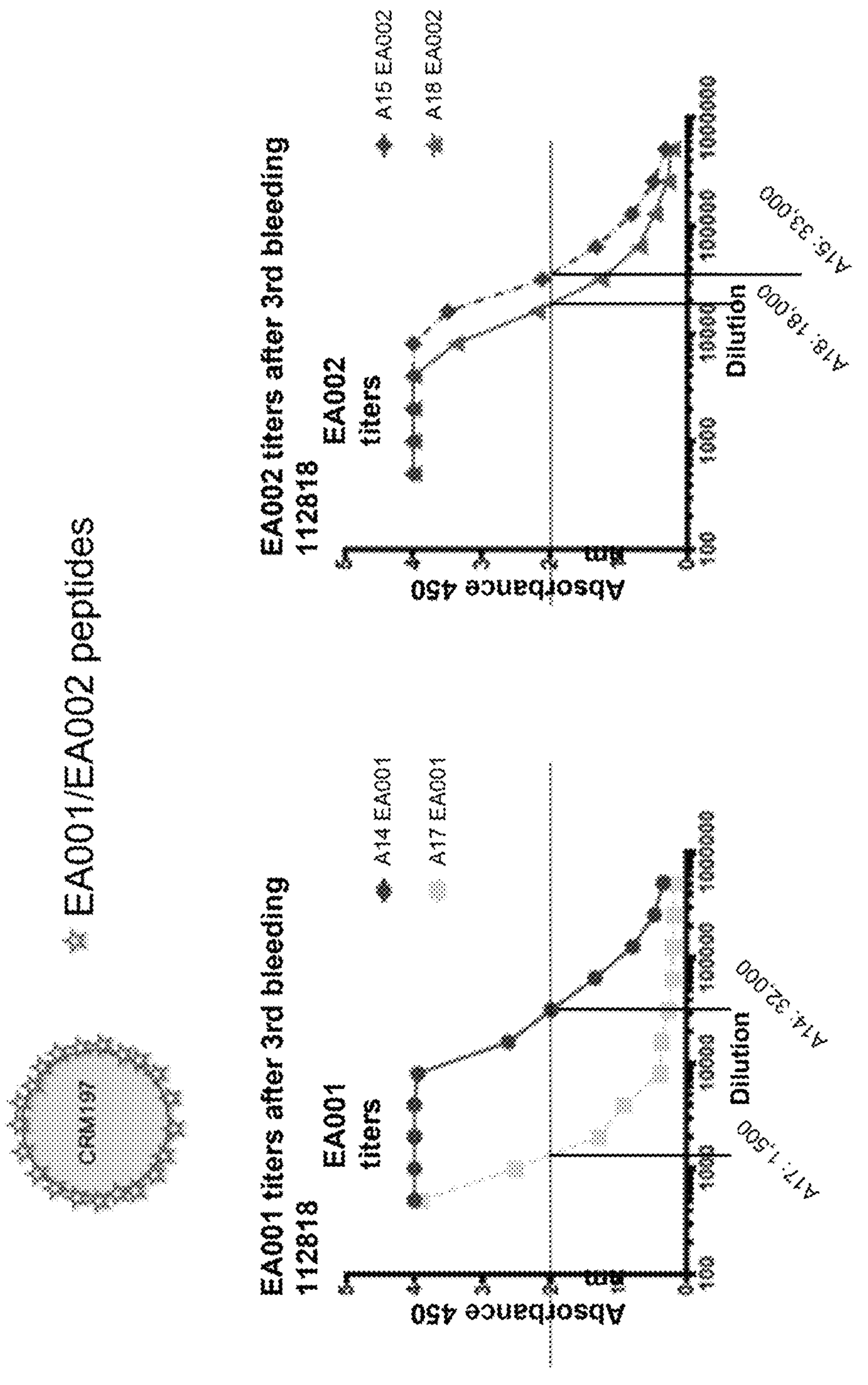
FIG. 1: Anti-ENG monoclonal antibody (mAb) identification targeting EA001/EA002 epitopes.

An isolated agonist anti-endoglin (ENG) coreceptor antibody, or anti-ENG coreceptor-binding agonist antibody fragment thereof.

In embodiments, the antibody or antibody fragment of the invention comprises one, two, or all three of the following heavy chain CDRs:

```
                    (SEQ ID NO: 3)
GFTFNTYA;

                    (SEQ ID NO: 4)
IRSKSSNYAT;

                    (SEQ ID NO: 5)
VRDRTGSWFAY.
```

In embodiments, the antibody or antibody fragment of the invention comprises one, two, or all three of the following light chain CDRs:

```
                    (SEQ ID NO: 6)
QDIGSS;

                    (SEQ ID NO: 7)
ATS;
```

-continued (SEQ ID NO: 8)
LQYASSPYT.

In embodiments, the antibody or antibody fragment of the invention comprises the following VH amino acid sequence:

(SEQ ID NO: 17)
EVQLVESGGGLVQPKGSLKLSCAASGFTFNTYAMHWVRQAPGKGLEWVA

RIRSKSSNYATYYADSVKDRFTISRDDSQSMLYLQMNNLKTEDTAMYYC

VRDRTGSWFAYWGQGTLVTVSA

In embodiments, the antibody or antibody fragment of the invention comprises the following VH amino acid sequence:

(SEQ ID NO: 9)
MVLGLKWVFFVVFYQGVHCEVQLVESGGGLVQPKGSLKLSCAASGFTFN

TYAMHWVRQAPGKGLEWVARIRSKSSNYATYYADSVKDRFTISRDDSQS

MLYLQMNNLKTEDTAMYYCVRDRTGSWFAYWGQGTLVTVSAESQSFPNV

FPLVSCESPLSDKNLVAMGCLARDFLPSTISFTWNYQNNTEVIQSIRTF

PTLRTGGKYLATSQVLLSPKSI

In embodiments, the antibody or antibody fragment of the invention comprises a VH sequence encoded by the following nucleotide sequence:

(SEQ ID NO: 10)
ATGGTGTTGGGGCTTAAGTGGGTTTTCTTTGTTGTTTTTTATCAAGGTG

TGCATTGTGAGGTGCAGCTTGTTGAGTCTGGTGGAGGATTGGTGCAGCC

TAAAGGATCATTGAAACTCTCATGTGCCGCCTCTGGTTTCACCTTCAAT

ACCTATGCCATGCACTGGGTCCGCCAGGCTCCAGGAAAGGGTTTGGAAT

GGGTTGCTCGCATAAGAAGTAAAAGTAGTAATTATGCAACATATTATGC

CGATTCAGTGAAAGACAGATTCACCATCTCCAGAGATGATTCACAAAGC

ATGCTCTATCTGCAAATGAACAACCTGAAAACTGAGGACACAGCCATGT

ATTACTGTGTGAGAGATAGAACTGGGTCCTGGTTTGCTTACTGGGGCCA

AGGGACTCTGGTCACTGTCTCTGCAGAGAGTCAGTCCTTCCCAAATGTC

TTCCCCCTCGTCTCCTGCGAGAGCCCCCTGTCTGATAAGAATCTGGTGG

CCATGGGCTGCCTGGCCCGGGACTTCCTGCCCAGCACCATTTCCTTCAC

CTGGAACTACCAGAACAACACTGAAGTCATCCAGAGTATCAGAACCTTC

CCAACACTGAGGACAGGGGGCAAGTACCTAGCCACCTCGCAGGTCTTGC

TGTCTCCCAAGAGCATC.

In embodiments, the antibody or antibody fragment of the invention comprises the following VL amino acid sequence:

(SEQ ID NO: 18)
DIQMTQSPSSLSASLGERVSLTCRASQDIGSSLNWLQQEPDGTIKRLIY

ATSSLDSGVPKRFSGSRSGSDYSLTISSLESEDFVDYYCLQYASSPYTF

GGGTKLEIK.

In embodiments, the antibody or antibody fragment of the invention comprises the following VL amino acid sequence:

(SEQ ID NO: 11)
MRAPAQIFGFLLLLFPGTRCDIQMTQSPSSLSASLGERVSLTCRASQDI

GSSLNWLQQEPDGTIKRLIYATSSLDSGVPKRFSGSRSGSDYSLTISSL

ESEDFVDYYCLQYASSPYTFGGGTKLEIKRADAAPTVSIFPPSSEQLTS

GGASVVCFLNNFYPKDINVKWKIDGSERQNGVLNSWTDQDSKDSTYSMS

STLTLTK.

In embodiments, the antibody or antibody fragment of the invention comprises a VL sequence encoded by the following nucleotide sequence:

(SEQ ID NO: 12)
ATGAGGGCTCCTGCACAAATTTTTGGCTTCTTGTTGCTCTTGTTTCCAG

GTACCAGATGTGACATCCAGATGACCCAGTCTCCATCCTCCTTATCTGC

CTCTCTGGGAGAAAGAGTCAGTCTCACTTGTCGGGCAAGTCAGGACATT

GGTAGTAGCTTAAACTGGCTTCAGCAGGAACCAGATGGAACTATTAAAC

GCCTGATCTACGCCACATCCAGTTTAGATTCTGGTGTCCCCAAAAGGTT

CAGTGGCAGTAGGTCTGGGTCAGATTATTCTCTCACCATCAGCAGCCTT

GAGTCTGAAGATTTTGTAGACTATTACTGTCTACAATATGCTAGTTCTC

CGTACACGTTCGGAGGGGGGACCAAGCTGGAAATAAAACGGGCTGATGC

TGCACCAACTGTATCCATCTTCCCACCATCCAGTGAGCAGTTAACATCT

GGAGGTGCCTCAGTCGTGTGCTTCTTGAACAACTTCTACCCCAAAGACA

TCAATGTCAAGTGGAAGATTGATGGCAGTGAACGACAAAATGGCGTCCT

GAACAGTTGGACTGATCAGGACAGCAAAGACAGCACCTACAGCATGAGC

AGCACCCTCACGTTGACCAAG.

In embodiments, an ScFv is provided which has agonist activity at an endoglin coreceptor.

In embodiments, the ScFv is one of the following, wherein the encoding nucleotide sequences are set forth hereinbelow:

LH15: VL-15aa-VH-Fc;
HL15: VH-15aa-VL-Fc;
LH20: VL-20aa-VH-Fc;
HL20: VH-20aa-VL-Fc.

ScFv HL15

(SEQ ID NO: 13)
GATCACCGGCGAAGGAGGGCCACCATGGACCCCAAGGGCAGCCTGAGCTGGAGAA

TCCTGCTGTTCCTGAGCCTGGCCTTCGAGCTGAGCTACGGCGAGGTGCAGCTTGTT

GAGTCTGGTGGAGGATTGGTGCAGCCTAAAGGATCATTGAAACTCTCATGTGCCGC

CTCTGGTTTCACCTTCAATACCTATGCCATGCACTGGGTCCGCCAGGCTCCAGGAA

AGGGTTTGGAATGGGTTGCTCGCATAAGAAGTAAAAGTAGTAATTATGCAACATAT

-continued

TATGCCGATTCAGTGAAAGACAGATTCACCATCTCCAGAGATGATTCACAAAGCAT

GCTCTATCTGCAAATGAACAACCTGAAAACTGAGGACACAGCCATGTATTACTGTG

TGAGAGATAGAACTGGGTCCTGGTTTGCTTACTGGGGCCAAGGGACTCTGGTCACT

GTCTCTGCAGGAGGTGGCGGATCAGGTGGCGGAGGTTCTGGCGGTGGCGGTTCTG

ACATCCAGATGACCCAGTCTCCATCCTCCTTATCTGCCTCTCTGGGAGAAAGAGTC

AGTCTCACTTGTCGGGCAAGTCAGGACATTGGTAGTAGCTTAAACTGGCTTCAGCA

GGAACCAGATGGAACTATTAAACGCCTGATCTACGCCACATCCAGTTTAGATTCTG

GTGTCCCCAAAAGGTTCAGTGGCAGTAGGTCTGGGTCAGATTATTCTCTCACCATC

AGCAGCCTTGAGTCTGAAGATTTTGTAGACTATTACTGTCTACAATATGCTAGTTCT

CCGTACACGTTCGGAGGGGGGACCAAGCTGGAAATAAAAGACAAGACCCACACCT

GCCCTCCCTGCCCCGCCCCCGAGCTGCTGGGCGGACCCAGCGTGTTCCTGTTCCCTC

CCAAGCCCAAGGACACCCTGATGATCAGCCGCACCCCCGAGGTGACCTGCGTGGT

GGTGGACGTGAGCCACGAGGACCCCGAGGTGAAGTTCAACTGGTACGTGGACGGC

GTGGAGGTGCACAACGCCAAGACCAAGCCTCGGGAGGAGCAGTACAACTCCACCT

ACCGCGTGGTGAGCGTGCTGACCGTGCTGCACCAGGACTGGCTGAACGGCAAGGA

GTACAAGTGCAAGGTGAGCAACAAGGCCCTGCCCGCTCCCATCGAGAAGACCATC

AGCAAGGCCAAGGGCCAGCCCCGGGAGCCTCAGGTGTACACCCTGCCCCCCAGCC

GCGACGAGCTGACCAAGAACCAGGTGAGCCTGACCTGCCTGGTGAAGGGCTTCTA

CCCCTCCGACATCGCCGTGGAGTGGGAGAGCAACGGCCAGCCTGAGAACAACTAC

AAGACCACCCCTCCCGTGCTGGACAGCGATGGCAGCTTCTTCCTGTACAGCAAGCT

GACCGTGGACAAGTCCCGGTGGCAGCAGGGCAACGTGTTCAGCTGCAGCGTGATG

CACGAGGCCCTGCACAACCACTACACCCAGAAGAGCCTGAGCCTGAGCCCCGGAT

AGTGATCCCAGTGTCCCTAGCTGGCCAGA.

ScFv LH15

(SEQ ID NO: 14)

GATCACCGGCGAAGGAGGGCCACCATGGACCCCAAGGGCAGCCTGAGCTGGAGAA

TCCTGCTGTTCCTGAGCCTGGCCTTCGAGCTGAGCTACGGCGACATCCAGATGACC

CAGTCTCCATCCTCCTTATCTGCCTCTCTGGGAGAAAGAGTCAGTCTCACTTGTCGG

GCAAGTCAGGACATTGGTAGTAGCTTAAACTGGCTTCAGCAGGAACCAGATGGAA

CTATTAAACGCCTGATCTACGCCACATCCAGTTTAGATTCTGGTGTCCCCAAAAGG

TTCAGTGGCAGTAGGTCTGGGTCAGATTATTCTCTCACCATCAGCAGCCTTGAGTCT

GAAGATTTTGTAGACTATTACTGTCTACAATATGCTAGTTCTCCGTACACGTTCGGA

GGGGGGACCAAGCTGGAAATAAAAGGAGGTGGCGGATCAGGTGGCGGAGGTTCT

GGCGGTGGCGGTTCTGAGGTGCAGCTTGTTGAGTCTGGTGGAGGATTGGTGCAGCC

TAAAGGATCATTGAAACTCTCATGTGCCGCCTCTGGTTTCACCTTCAATACCTATGC

CATGCACTGGGTCCGCCAGGCTCCAGGAAAGGGTTTGGAATGGGTTGCTCGCATAA

GAAGTAAAAGTAGTAATTATGCAACATATTATGCCGATTCAGTGAAAGACAGATTC

ACCATCTCCAGAGATGATTCACAAAGCATGCTCTATCTGCAAATGAACAACCTGAA

AACTGAGGACACAGCCATGTATTACTGTGTGAGAGATAGAACTGGGTCCTGGTTTG

CTTACTGGGGCCAAGGGACTCTGGTCACTGTCTCTGCAGACAAGACCCACACCTGC

-continued

CCTCCCTGCCCCGCCCCCGAGCTGCTGGGCGGACCCAGCGTGTTCCTGTTCCCTCCC

AAGCCCAAGGACACCCTGATGATCAGCCGCACCCCCGAGGTGACCTGCGTGGTGG

TGGACGTGAGCCACGAGGACCCCGAGGTGAAGTTCAACTGGTACGTGGACGGCGT

GGAGGTGCACAACGCCAAGACCAAGCCTCGGGAGGAGCAGTACAACTCCACCTAC

CGCGTGGTGAGCGTGCTGACCGTGCTGCACCAGGACTGGCTGAACGGCAAGGAGT

ACAAGTGCAAGGTGAGCAACAAGGCCCTGCCCGCTCCCATCGAGAAGACCATCAG

CAAGGCCAAGGGCCAGCCCCGGGAGCCTCAGGTGTACACCCTGCCCCCCAGCCGC

GACGAGCTGACCAAGAACCAGGTGAGCCTGACCTGCCTGGTGAAGGGCTTCTACC

CCTCCGACATCGCCGTGGAGTGGGAGAGCAACGGCCAGCCTGAGAACAACTACAA

GACCACCCCTCCCGTGCTGGACAGCGATGGCAGCTTCTTCCTGTACAGCAAGCTGA

CCGTGGACAAGTCCCGGTGGCAGCAGGGCAACGTGTTCAGCTGCAGCGTGATGCA

CGAGGCCCTGCACAACCACTACACCCAGAAGAGCCTGAGCCTGAGCCCCGGATAG

TGATCCCAGTGTCCCTAGCTGGCCAGA.

ScFv HL20

(SEQ ID NO: 15)

GATCACCGGCGAAGGAGGGCCACCATGGACCCCAAGGGCAGCCTGAGCTGGAGAA

TCCTGCTGTTCCTGAGCCTGGCCTTCGAGCTGAGCTACGGCGAGGTGCAGCTTGTT

GAGTCTGGTGGAGGATTGGTGCAGCCTAAAGGATCATTGAAACTCTCATGTGCCGC

CTCTGGTTTCACCTTCAATACCTATGCCATGCACTGGGTCCGCCAGGCTCCAGGAA

AGGGTTTGGAATGGGTTGCTCGCATAAGAAGTAAAAGTAGTAATTATGCAACATAT

TATGCCGATTCAGTGAAAGACAGATTCACCATCTCCAGAGATGATTCACAAAGCAT

GCTCTATCTGCAAATGAACAACCTGAAAACTGAGGACACAGCCATGTATTACTGTG

TGAGAGATAGAACTGGGTCCTGGTTTGCTTACTGGGGCCAAGGGACTCTGGTCACT

GTCTCTGCAGGCTCTACAGGAGGTGGCGGATCAGGTAAACCTGGTTCTGGCGAAG

GAGGTGGCGGTTCAGACATCCAGATGACCCAGTCTCCATCCTCCTTATCTGCCTCTC

TGGGAGAAAGAGTCAGTCTCACTTGTCGGGCAAGTCAGGACATTGGTAGTAGCTTA

AACTGGCTTCAGCAGGAACCAGATGGAACTATTAAACGCCTGATCTACGCCACATC

CAGTTTAGATTCTGGTGTCCCCAAAAGGTTCAGTGGCAGTAGGTCTGGGTCAGATT

ATTCTCTCACCATCAGCAGCCTTGAGTCTGAAGATTTTGTAGACTATTACTGTCTAC

AATATGCTAGTTCTCCGTACACGTTCGGAGGGGGGACCAAGCTGGAAATAAAAGA

CAAGACCCACACCTGCCCTCCCTGCCCCGCCCCCGAGCTGCTGGGCGGACCCAGCG

TGTTCCTGTTCCCTCCCAAGCCCAAGGACACCCTGATGATCAGCCGCACCCCCGAG

GTGACCTGCGTGGTGGTGGACGTGAGCCACGAGGACCCCGAGGTGAAGTTCAACT

GGTACGTGGACGGCGTGGAGGTGCACAACGCCAAGACCAAGCCTCGGGAGGAGCA

GTACAACTCCACCTACCGCGTGGTGAGCGTGCTGACCGTGCTGCACCAGGACTGGC

TGAACGGCAAGGAGTACAAGTGCAAGGTGAGCAACAAGGCCCTGCCCGCTCCCAT

CGAGAAGACCATCAGCAAGGCCAAGGGCCAGCCCCGGGAGCCTCAGGTGTACACC

CTGCCCCCCAGCCGCGACGAGCTGACCAAGAACCAGGTGAGCCTGACCTGCCTGG

TGAAGGGCTTCTACCCCTCCGACATCGCCGTGGAGTGGGAGAGCAACGGCCAGCC

TGAGAACAACTACAAGACCACCCCTCCCGTGCTGGACAGCGATGGCAGCTTCTTCC

-continued

TGTACAGCAAGCTGACCGTGGACAAGTCCCGGTGGCAGCAGGGCAACGTGTTCAG

CTGCAGCGTGATGCACGAGGCCCTGCACAACCACTACACCCAGAAGAGCCTGAGC

CTGAGCCCCGGATAGTGATCCCAGTGTCCCTAGCTGGCCAGA.

ScFv LH20

(SEQ ID NO: 16)

GATCACCGGCGAAGGAGGGCCACCATGGACCCCAAGGGCAGCCTGAGCTGGAGAA

TCCTGCTGTTCCTGAGCCTGGCCTTCGAGCTGAGCTACGGCGACATCCAGATGACC

CAGTCTCCATCCTCCTTATCTGCCTCTCTGGGAGAAAGAGTCAGTCTCACTTGTCGG

GCAAGTCAGGACATTGGTAGTAGCTTAAACTGGCTTCAGCAGGAACCAGATGGAA

CTATTAAACGCCTGATCTACGCCACATCCAGTTTAGATTCTGGTGTCCCCAAAAGG

TTCAGTGGCAGTAGGTCTGGGTCAGATTATTCTCTCACCATCAGCAGCCTTGAGTCT

GAAGATTTTGTAGACTATTACTGTCTACAATATGCTAGTTCTCCGTACACGTTCGGA

GGGGGGACCAAGCTGGAAATAAAAGGCTCTACAGGAGGTGGCGGATCAGGTAAA

CCTGGTTCTGGCGAAGGAGGTGGCGGTTCAGAGGTGCAGCTTGTTGAGTCTGGTGG

AGGATTGGTGCAGCCTAAAGGATCATTGAAACTCTCATGTGCCGCCTCTGGTTTCA

CCTTCAATACCTATGCCATGCACTGGGTCCGCCAGGCTCCAGGAAAGGGTTTGGAA

TGGGTTGCTCGCATAAGAAGTAAAAGTAGTAATTATGCAACATATTATGCCGATTC

AGTGAAAGACAGATTCACCATCTCCAGAGATGATTCACAAAGCATGCTCTATCTGC

AAATGAACAACCTGAAAACTGAGGACACAGCCATGTATTACTGTGTGAGAGATAG

AACTGGGTCCTGGTTTGCTTACTGGGGCCAAGGGACTCTGGTCACTGTCTCTGCAG

ACAAGACCCACACCTGCCCTCCCTGCCCCGCCCCCGAGCTGCTGGGCGGACCCAGC

GTGTTCCTGTTCCCTCCCAAGCCCAAGGACACCCTGATGATCAGCCGCACCCCCGA

GGTGACCTGCGTGGTGGTGGACGTGAGCCACGAGGACCCCGAGGTGAAGTTCAAC

TGGTACGTGGACGGCGTGGAGGTGCACAACGCCAAGACCAAGCCTCGGGAGGAGC

AGTACAACTCCACCTACCGCGTGGTGAGCGTGCTGACCGTGCTGCACCAGGACTGG

CTGAACGGCAAGGAGTACAAGTGCAAGGTGAGCAACAAGGCCCTGCCCGCTCCCA

TCGAGAAGACCATCAGCAAGGCCAAGGGCCAGCCCCGGGAGCCTCAGGTGTACAC

CCTGCCCCCCAGCCGCGACGAGCTGACCAAGAACCAGGTGAGCCTGACCTGCCTG

GTGAAGGGCTTCTACCCCTCCGACATCGCCGTGGAGTGGGAGAGCAACGGCCAGC

CTGAGAACAACTACAAGACCACCCCTCCCGTGCTGGACAGCGATGGCAGCTTCTTC

CTGTACAGCAAGCTGACCGTGGACAAGTCCCGGTGGCAGCAGGGCAACGTGTTCA

GCTGCAGCGTGATGCACGAGGCCCTGCACAACCACTACACCCAGAAGAGCCTGAG

CCTGAGCCCCGGATAGTGATCCCAGTGTCCCTAGCTGGCCAGA.

In embodiments, the ScFv sequences SEQ ID NOS:13-16 herein include: signal peptide sequence, variable region sequence of light chain, variable region sequence of heavy chain, linker sequence, Fc region sequence of human IgG1, and vector sequence.

In embodiments, the ScFv comprises SEQ ID NO:17 and SEQ ID NO:18. In embodiments, the ScFv is an agonist at an ENG coreceptor and comprises at least one of SEQ ID NO:17 and SEQ ID NO:18. In embodiments, the ScFv is an agonist at an ENG coreceptor and comprises SEQ ID NOS:3-5 and 6-8.

An antibody or antigen-binding fragment thereof comprising a heavy chain comprising one or more of:

(SEQ ID NO: 3)

GFTFNTYA;

(SEQ ID NO: 4)

IRSKSSNYAT;

-continued

```
                              (SEQ ID NO: 5)
VRDRTGSWFAY;
```

and a light chain comprising one or more of:

```
                              (SEQ ID NO: 6)
QDIGSS;

                              (SEQ ID NO: 7)
ATS;

                              (SEQ ID NO: 8)
LQYASSPYT.
```

An antibody or antigen-binding fragment thereof which binds to an endoglin (ENG) coreceptor and comprises:

a heavy chain comprising each of the following CDRs:

```
                              (SEQ ID NO: 3)
GFTFNTYA;

                              (SEQ ID NO: 4)
IRSKSSNYAT;

                              (SEQ ID NO: 5)
VRDRTGSWFAY;
```

and a light chain comprising one or more of the following CDRs:

```
                              (SEQ ID NO: 6)
QDIGSS;

                              (SEQ ID NO: 7)
ATS;

                              (SEQ ID NO: 8)
LQYASSPYT.
```

An antibody or antigen-binding fragment thereof which binds to a human endoglin coreceptor.

In embodiments, the antibody or antigen-binding fragment thereof is agonistic at an endoglin (ENG) coreceptor.

In embodiments, the antibody is a monoclonal antibody.

An antibody or antigen-binding fragment thereof which binds to and is agonistic at an endoglin coreceptor and comprises a heavy chain encoded by SEQ ID NO:10.

An antibody or antigen-binding fragment thereof which binds to and is agonistic at an endoglin coreceptor and comprises a heavy chain having SEQ ID NO:17.

An antibody or antigen-binding fragment thereof which binds to and is agonistic at an endoglin coreceptor and comprises a light chain encoded by SEQ ID NO:12.

An antibody or antigen-binding fragment thereof which binds to and is agonistic at an endoglin coreceptor and comprises a light chain having SEQ ID NO:18.

An ScFv encoded by the nucleotide sequence set forth in one of SEQ ID NOs:13, 14, 15 or 16. An ScFv comprising SEQ ID NO:17 and SEQ ID NO:18. In embodiments, the ScFv binds to and is agonistic at an endoglin coreceptor.

An isolated agonist endoglin coreceptor antibody or antibody fragment that: specifically binds to the epitope set forth in SEQ ID NO:1 or SEQ ID NO:2, the antibody or antibody fragment comprising a heavy chain variable region comprising the CDR sequences set forth in SEQ ID NOs:3-5; and/or a light chain variable region comprising the CDR sequences set forth in SEQ ID NOs:6-8; or cross-competes for specific binding with a reference antibody to the epitope set forth in SEQ ID NO:1 or SEQ ID NO:2, the reference antibody comprising a heavy chain variable region comprising the CDR sequences set forth in SEQ ID NOs:3-5; and/or a light chain variable region comprising the CDR sequences set forth in SEQ ID NOs:6-8.

In embodiments, the antibody or antigen-binding fragment thereof is agonistic when bound to an endoglin coreceptor.

In embodiments, the antibody or antigen-binding fragment thereof effectuates endothelial SMAD1/SMAD5/SMAD8 signaling when bound to an ENG co-receptor.

In embodiments, the antibody or antigen-binding fragment thereof phosphorylates at least one of endothelial SMAD1, SMAD5 and SMAD8 when bound to an ENG co-receptor.

In embodiments, the antibody or antigen-binding fragment thereof phosphorylates all of endothelial SMAD1, SMAD5 and SMAD8 when bound to an ENG co-receptor.

In embodiments, the antibody or antigen-binding fragment thereof activates activin receptor-like kinase 1 (ALK1) signaling or ALK1-ENG-BMPR2 receptor activation when bound to an ENG co-receptor.

In embodiments, the antibody or antigen-binding fragment thereof activates Notch signaling when bound to an ENG co-receptor.

In embodiments, the antibody or antigen-binding fragment thereof activates Notch signaling via an endoglin/ALK1 receptor complex.

In embodiments, the antibody or antigen-binding fragment thereof increases Notch ligand Dll4 levels in a cell and/or elicits generation of Notch activated fragment NICD.

In embodiments, the antibody or antigen-binding fragment thereof comprises framework regions of the light chain and/or the heavy chain which are human framework regions, or have 85% or more identity thereto. In embodiments, the antibody or antigen-binding fragment thereof comprises framework regions of the light chain and/or the heavy chain which have 86, 87, 88, 89, 90, 91, 92, 93, 94, 95, 96, 97, 98, or 99% or more identity thereto.

In embodiments, the antibody or antigen-binding fragment thereof comprise framework regions of the light chain and/or the heavy chain which are human framework regions.

In embodiments, the antibody disclosed herein is provided. In embodiments, the antigen-binding fragment of the antibody disclosed herein is provided.

In embodiments, the antibody disclosed herein is an IgM.

In embodiments, the antibody or antigen-binding fragment thereof binds a BMP9-binding region within an ectodomain of the ENG coreceptor.

In embodiments, the antibody or antigen-binding fragment thereof binds an epitope comprising SEQ ID NO:1 or SEQ ID NO:2 of the ENG coreceptor.

In embodiments, the antibody or antigen-binding fragment thereof binds to an ENG coreceptor, or a BMP9-binding region within an ectodomain of an ENG coreceptor, with an affinity of 1.5 nM $K_D$ or stronger.

In embodiments, the antibody or antigen-binding fragment thereof binds to an ENG coreceptor, or a BMP9-binding region within an ectodomain of an ENG coreceptor, with an affinity of 0.75 nM $K_D$ or stronger.

In embodiments, the antibody or antigen-binding fragment thereof comprises a human sequence Fc region.

In embodiments, the antibody or antigen-binding fragment thereof is chimeric or humanized.

In embodiments, the antibody or antigen-binding fragment thereof is selected from the group consisting of a monoclonal antibody, an Fab fragment, an Fab' fragment, an F(ab)' fragment and a bispecific antibody. In embodiments, the antigen-binding fragment thereof is a fusion protein. In embodiments, the antigen-binding fragment thereof is a fusion protein and is an ScFv.

In embodiments, the antibody or antigen-binding fragment thereof is linked or conjugated to a therapeutic agent, an imaging agent or a detectable marker. In embodiments, the therapeutic agent is a cytotoxic drug, a radioactive isotope, an immunomodulator, or a second antibody.

In embodiments, the isolated agonist anti-ENG coreceptor antibody, or anti-ENG coreceptor-binding agonist antibody fragment thereof, effectuates endothelial SMAD1/SMAD5/SMAD8 signaling when bound to an ENG co-receptor.

In embodiments, the isolated agonist anti-ENG coreceptor antibody, or anti-ENG coreceptor-binding agonist antibody fragment thereof, phosphorylates at least one of endothelial SMAD1, SMAD5 and SMAD8 when bound to an ENG co-receptor.

In embodiments, the isolated agonist anti-ENG coreceptor antibody, or anti-ENG coreceptor-binding agonist antibody fragment thereof, phosphorylates all of endothelial SMAD1, SMAD5 and SMAD8 when bound to an ENG co-receptor.

In embodiments, the isolated agonist anti-ENG coreceptor antibody, or anti-ENG coreceptor-binding agonist antibody fragment thereof, activates activin receptor-like kinase 1 (ALK1) signaling or ALK1-ENG-BMPR2 receptor activation when bound to an ENG co-receptor.

In embodiments, the isolated agonist anti-ENG coreceptor antibody, or anti-ENG coreceptor-binding agonist antibody fragment thereof comprises framework regions of the light chain and/or the heavy chain which are human framework regions, or have 85, 86, 87, 88, 89, 90, 91, 92, 93, 94, 95, 96, 97, 98 or 99% or more identity thereto.

In embodiments, the isolated agonist anti-ENG coreceptor antibody, or anti-ENG coreceptor-binding agonist antibody fragment thereof comprises framework regions of the light chain and/or the heavy chain which are human framework regions.

In embodiments, the isolated agonist anti-ENG coreceptor antibody is claimed. In embodiments, the anti-ENG coreceptor-binding agonist antibody fragment thereof is claimed.

In embodiments, the isolated agonist anti-ENG coreceptor antibody is an IgM, or the anti-ENG coreceptor-binding agonist antibody fragment thereof is a fragment of an IgM.

In embodiments, the isolated agonist anti-ENG coreceptor antibody, or anti-ENG coreceptor-binding agonist antibody fragment thereof, binds a bone morphogenic protein 9 (BMP9)-binding region within an ectodomain of the ENG coreceptor.

In embodiments, the isolated agonist anti-ENG coreceptor antibody, or anti-ENG coreceptor-binding agonist antibody fragment thereof, binds an epitope comprising SEQ ID NO:1 or SEQ ID NO:2 of the ENG coreceptor.

In embodiments, the epitope comprises TTGEYSFKIFP (SEQ ID NO:1). In embodiments, the epitope TTGEYSVKIFP (SEQ ID NO:2).

In embodiments, the ENG coreceptor is a human ENG coreceptor. In embodiments, the BMP9 is a human BMP9.

In embodiments, the antibody comprises framework regions, and the framework regions of the light chain and the heavy chain are human framework regions, or have 85% or more identity thereto. In embodiments, framework regions of the light chain and the heavy chain are human framework regions. In embodiments, the antibody, isolated antibody or antigen-binding fragment thereof is chimeric or humanized.

In embodiments, the antibody, isolated antibody or antigen-binding fragment thereof is selected from the group consisting of a monoclonal antibody, an Fab fragment, an Fab' fragment, and an F(ab)' fragment.

In embodiments, the antibody or fragment thereof is selected from the group consisting of a monoclonal antibody, an scFv, an Fab fragment, an Fab' fragment, and an F(ab)' fragment.

In embodiments, the agonist anti-ENG coreceptor antibody or ENG coreceptor-binding agonist fragment thereof (i.e., an antigen-binding fragment thereof), comprises (i) a VH framework comprising the framework sequence of human germline IGHV1-2*02, IGHV1-2*03, IGHV1-2*04, IGHV1-2*05, IGHV1-2*06, IGHV1-18*04, IGHV1-69-2*01, IGHV1-46*01, IGHV7-4-1*01, IGHV7-4-1*02, IGHV7-4-1*01, IGHV7-81*01, IGHD2-8*02, IGHD3-10*01, IGHD3-10*02, IGHD3-22*01, IGHD5-18*01, IGHD5-5*01, IGHD5-12*01, IGHD5-24*01, IGHD6-25*01, IGHJ3*01, IGHJ4*01, IGHJ4*02, IGHJ4*03, IGHJ6*01, IGHJ6*02 and/or (ii) a VL framework comprising the framework sequence of human germline IGKV1-17*01, IGKV1-6*01, IGKV1-6*02, IGKV1-13*02, IGKV1-27*01, IGKV1-33*01, IGKV3-7*02, IGKV4-1*01, IGKV1D-13*02, IGKV1D-33*01, IGKV3D-7*01, IGKJ1*01, IGKJ2*01, IGKJ3*01, IGKJ4*01, IGKJ4*02.

In embodiments, the agonist anti-ENG coreceptor antibody or ENG coreceptor-binding agonist fragment thereof, binds ENG coreceptor with a binding affinity ($K_D$) of from about $1\times10^{-9}$M to about $1\times10^{-12}$ M.

An isolated antibody or antigen-binding fragment thereof which binds to an ENG coreceptor, or a bone morphogenic protein 9 (BMP9)-binding region within an ectodomain of an ENG coreceptor, with an affinity of 1.5 nM $K_D$ or stronger.

In embodiments, the isolated antibody or antigen-binding fragment thereof binds to an ENG coreceptor, or a BMP9-binding region within an ectodomain of an ENG coreceptor, with an affinity of 0.75 nM $K_D$ or stronger.

In embodiments, the isolated antibody or antigen-binding fragment thereof comprises a human sequence Fc region.

In embodiments, the isolated antibody or antigen-binding fragment thereof is chimeric or humanized.

In embodiments, the isolated antibody or antigen-binding fragment thereof is selected from the group consisting of a monoclonal antibody, an scFv, an Fab fragment, an Fab' fragment, an F(ab)' fragment and a bispecific antibody.

A nucleic acid encoding a heavy chain of an agonist anti-endoglin (ENG) coreceptor antibody or fragment thereof described herein. A nucleic acid encoding a light chain of an agonist anti-endoglin (ENG) coreceptor antibody or fragment thereof described herein. In an embodiment, the nucleic acid is a DNA. In an embodiment, the nucleic acid is a cDNA. In an embodiment, the nucleic acid is an RNA.

A nucleic acid encoding a heavy chain of an antibody which comprises one or more of:

```
                                   (SEQ ID NO: 3)
GFTFNTYA;
                                   (SEQ ID NO: 4)
IRSKSSNYAT;
                                   (SEQ ID NO: 5)
VRDRTGSWFAY;
```

A nucleic acid encoding a light chain of an antibody which comprises one or more of:

(SEQ ID NO: 6)
QDIGSS;

(SEQ ID NO: 7)
ATS;

(SEQ ID NO: 8)
LQYASSPYT.

A vector encoding the nucleic acid molecule described herein is provided.

A host cell comprising the nucleic acid molecule described herein, or the vector described herein, is provided.

A hybridoma which produces an agonist anti-ENG coreceptor monoclonal antibody of the invention, which antibody is described herein, is also provided.

An agonist anti-endoglin (ENG) coreceptor antibody or fragment thereof described herein, linked or conjugated to a therapeutic agent, an imaging agent or a detectable marker. In embodiments, the therapeutic agent is a cytotoxic drug, a radioactive isotope, an immunomodulator, or a second antibody.

A method of producing the antibody or fragment thereof of the invention, comprising culturing the host cell described herein, under conditions wherein the agonist anti-ENG coreceptor antibody, or fragment thereof, is produced by the host cell.

A method of detecting an ENG coreceptor-positive cell in a subject or a sample comprising administering to the subject, or contacting the sample with, an amount of an agonist anti-endoglin (ENG) coreceptor antibody or fragment thereof described herein having a detectable marker conjugated thereto, in an amount effective to label an ENG coreceptor-positive cell and then detecting the presence of and/or quantifying the level of the label in the subject, thereby detecting an ENG coreceptor-positive cell in the subject or the sample.

In embodiments, the label is detected by imaging. In embodiments, the cell is an endothelial cell.

A pharmaceutical composition comprising an amount of the isolated agonist anti-endoglin (ENG) coreceptor antibody or fragment thereof described herein and a pharmaceutically acceptable carrier or excipient.

A method of detecting an ENG coreceptor-positive cell in a subject or a sample comprising administering to the subject, or contacting the sample with, an amount of an antibody or ENG coreceptor binding fragment thereof as provided herein, having a detectable marker conjugated thereto, in an amount effective to label an ENG coreceptor-positive cell and then detecting the presence of and/or quantifying the level of the label in the subject, thereby detecting an ENG coreceptor-positive cell in the subject or the sample.

In embodiments, the label is detected by imaging. In embodiments, the cell is an endothelial cell.

In embodiments, the antibody or antigen-binding fragment thereof is synthetically made by, e.g., a hybridoma or recombinant means.

A pharmaceutical composition comprising an amount of an antibody or ENG coreceptor-binding fragment thereof as provided herein, and a pharmaceutically acceptable carrier or excipient.

A method of treating hereditary hemorrhagic telangiectasia or preventing one or more symptoms of hereditary hemorrhagic telangiectasia in a subject comprising administering to the subject an amount of an antibody or ENG coreceptor binding-fragment thereof as provided herein, or a composition comprising such, effective to treat or prevent one or more symptoms of hereditary hemorrhagic telangiectasia.

A method of treating pulmonary arterial hypertension or preventing one or more symptoms of pulmonary arterial hypertension in a subject comprising administering to the subject an amount of an antibody or ENG coreceptor binding-fragment thereof as provided herein, or a composition comprising such, effective to treat or prevent one or more symptoms of pulmonary arterial hypertension.

A method of activating activin receptor-like kinase 1 (ALK1) signaling or ALK1-ENG-BMPR2 receptor activation by an ENG co-receptor comprising contacting the ENG co-receptor with an amount of an antibody or ENG coreceptor binding fragment thereof as provided herein.

A method of effecting phosphorylation of at least one of endothelial SMAD1, SMAD5 and SMAD8 associated with activation of an ENG co-receptor comprising contacting the ENG co-receptor with an amount of an antibody or ENG coreceptor-binding fragment thereof as provided herein.

In embodiments, the method is used to prevent or treat a disease or disorder that is associated with reduced phosphorylation of endothelial SMAD1, SMAD5 and/or SMAD8 in a subject.

In embodiments, the disease or disorder is hereditary hemorrhagic telangiectasia.

In embodiments, the disease or disorder is pulmonary arterial hypertension.

A method of treating a cancer in a subject comprising administering to the subject an amount of an antibody or ENG coreceptor-binding fragment thereof as provided herein, or a composition comprising such, effective to treat a cancer in a subject.

In embodiment, the cancer is associated with Notch loss-of-function.

In embodiments, the cancer is head and neck squamous cell carcinoma (HNSCC), squamous cancer of the skin, squamous cancer of the lung, or squamous cancer of the esophagus.

In embodiments, the cancer is squamous cancer of the lung.

In embodiments of the methods, the subject is a mammal.

In embodiments of the methods, the mammal is a human.

A method of treating hereditary hemorrhagic telangiectasia or preventing one or more symptoms of hereditary hemorrhagic telangiectasia in a subject comprising administering to the subject an amount of an agonist anti-endoglin (ENG) coreceptor antibody or fragment thereof described herein, or a composition comprising such, effective to treat or prevent one or more symptoms of hereditary hemorrhagic telangiectasia.

In embodiments, the method is to treat or prevent a symptom of HHT1. In embodiments, the method is to treat or prevent a symptom of HHT2. In embodiments, the method is to treat the hereditary hemorrhagic telangiectasia. In embodiments, the method is to prevent one or more symptoms of the hereditary hemorrhagic telangiectasia.

A method of treating pulmonary arterial hypertension or preventing one or more symptoms of pulmonary arterial hypertension in a subject comprising administering to the subject an amount of an agonist anti-endoglin (ENG) coreceptor antibody or fragment thereof described herein, or a composition comprising such, effective to treat or prevent one or more symptoms of pulmonary arterial hypertension (PAH).

In embodiments, the method is to treat the pulmonary arterial hypertension. In embodiments, the method is to prevent one or more symptoms of the pulmonary arterial hypertension. In embodiments, the pulmonary arterial hypertension is familial pulmonary arterial hypertension.

A method of activating activin receptor-like kinase 1 (ALK1) signaling or ALK1-ENG-BMPR2 receptor activation by an ENG co-receptor comprising contacting the ENG co-receptor with an agonist anti-endoglin (ENG) coreceptor antibody or fragment thereof described herein.

A method of effecting phosphorylation of at least one of endothelial SMAD1, SMAD5 and SMAD8 associated with activation of an ENG co-receptor comprising contacting the ENG co-receptor with an amount of an agonist anti-endoglin (ENG) coreceptor antibody or fragment thereof described herein.

In embodiments, the method is used to prevent or treat a disease or disorder that is associated with reduced phosphorylation of endothelial SMAD1, SMAD5 and/or SMAD8 in a subject.

In embodiments, the disease or disorder is hereditary hemorrhagic telangiectasia.

In embodiments, the disease or disorder is pulmonary arterial hypertension.

A method of activating a Notch signaling pathway in a subject comprising administering to the subject an amount of an agonist anti-ENG coreceptor antibody or ENG coreceptor-binding fragment thereof, or a composition comprising such, effective to activate a Notch signaling pathway in a subject. In embodiments, the method effects an increase of a cellular Notch ligand Dll4 level and/or elicits generation of Notch activated fragment NICD in the subject.

In embodiments of the methods herein, the subject is a mammal.

In embodiments of the methods herein, the mammal is a human.

Use of an effective amount of an agonist anti-ENG coreceptor antibody or fragment thereof described herein for the manufacture of a medicament for treating, or preventing a symptom of, hereditary hemorrhagic telangiectasia.

Use of an effective amount of an agonist anti-ENG coreceptor antibody or fragment thereof described herein for the manufacture of a medicament for treating or preventing pulmonary arterial hypertension.

Use of an effective amount of an agonist anti-ENG coreceptor antibody or fragment thereof described herein for the manufacture of a medicament for treating or preventing a squamous cell cancer.

As used herein, the term "antibody" refers to an intact antibody, i.e., with complete Fc and Fv regions. "Fragment" refers to any portion of an antibody, or in embodiments portions of an antibody linked together, such as, in non-limiting examples, a Fab, F(ab)2, a single-chain Fv (scFv), which is less than the whole antibody but which is an antigen-binding portion and which competes with the intact antibody of which it is a fragment for specific binding. In this case, the antigen is the ENG coreceptor. In an embodiment, the fragment is an actual fragment of an antibody. In an embodiment, the fragment is a fusion protein, which, in further embodiments is an ScFv. In an embodiment the antibody, or fragment thereof, binds the BMP9-binding region (bone morphogenic protein 9-binding region) within an ectodomain of the ENG coreceptor. In an embodiment, the antigen is the BMP9-binding region (bone morphogenic protein 9-binding region) within an ectodomain of the ENG coreceptor. In an embodiment, the antigen is SEQ ID NO:1 or 2. In an embodiment, the antibody or fragment binding to the ENG coreceptor causes activation of the ENG coreceptor.

An "antibody" or a "fragment" thereof can comprise an immunoglobulin of any class, e.g., IgM, IgG, IgA, IgD and IgE. In some embodiments, the term "antibody" or a "fragment" thereof encompasses not only intact polyclonal or monoclonal antibodies, but also fragments thereof (such as Fab, Fab', F(ab')2, Fv), single chain (ScFv), mutants thereof, naturally occurring variants, fusion proteins comprising an antibody portion with an antigen recognition site of the required specificity, humanized antibodies, chimeric antibodies, and any other modified configuration of the immunoglobulin molecule that comprises an antigen recognition site of the required specificity.

Such fragments can be prepared, for example, by cleaving an intact antibody or by recombinant means. See generally, Fundamental Immunology, Ch. 7 (Paul, W., ed., 2nd ed. Raven Press, N.Y. (1989), hereby incorporated by reference in its entirety). Antigen-binding fragments may be produced by recombinant DNA techniques or by enzymatic or chemical cleavage of intact antibodies or by molecular biology techniques. In some embodiments, a fragment is an Fab, Fab', F(ab')2, Fd, Fv, complementarity determining region (CDR) fragment.

In embodiments, the fragment is a single-chain variable fragment (ScFv; a variable domain light chain (VL) and a variable domain heavy chain (VH) linked via a peptide linker). In an embodiment, the ScFv comprises a variable domain framework sequence having a sequence identical to a human variable domain FR1, FR2, FR3 or FR4. In an embodiment, the ScFv comprises a linker peptide from 5 to 30 amino acid residues long. In an embodiment, the ScFv comprises a linker peptide comprising one or more of glycine, serine and threonine residues. In an embodiment the linker of the scFv is 10-25 amino acids in length. In an embodiment the peptide linker comprises glycine, serine and/or threonine residues. For example, see Bird et al., Science, 242: 423-426 (1988) and Huston et al., Proc. Natl. Acad. Sci. USA, 85:5879-5883 (1988) each of which are hereby incorporated by reference in their entirety), or a polypeptide that contains at least a portion of an antibody that is sufficient to confer ENG coreceptor specific antigen binding on the polypeptide, including a diabody. From N-terminus to C-terminus, both the mature light and heavy chain variable domains comprise the regions FR1, CDR1, FR2, CDR2, FR3, CDR3 and FR4. The assignment of amino acids to each domain is in accordance with the definitions of Kabat, Sequences of Proteins of Immunological Interest (National Institutes of Health, Bethesda, Md. (1987 and 1991), Chothia & Lesk, J. Mol. Biol. 196:901-917 (1987), or Chothia et al., Nature 342:878-883 (1989), each of which are hereby incorporated by reference in their entirety). As used herein, the term "polypeptide" encompasses native or artificial proteins, protein fragments and polypeptide analogs of a protein sequence. A polypeptide may be monomeric or polymeric. As used herein, an Fd fragment means an antibody fragment that consists of the VH and CH1 domains; an Fv fragment consists of the V1 and VH domains of a single arm of an antibody; and a dAb fragment (Ward et al., Nature 341:544-546 (1989) hereby incorporated by reference in its entirety) consists of a VH domain. In some embodiments, fragments are at least 5, 6, 8 or 10 amino acids long. In other embodiments, the fragments are at least 14, at least 20, at least 50, or at least 70, 80, 90, 100, 150 or 200 amino acids long.

The term "monoclonal antibody" as used herein refers to an antibody member of a population of substantially homogeneous antibodies, i.e., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins. Thus, an identified monoclonal antibody can be produced by non-hybridoma techniques, e.g., by appropriate recombinant means once the sequence thereof is identified. For example, other than hybridoma techniques, antibodies of the invention can be produced by cells transfected with an immortalizing virus, or by production in an immortal cell culture line (such as Chinese hamster ovary (CHO) cells).

In an embodiment of the inventions described herein, the antibody is isolated. As used herein, the term "isolated antibody" refers to an antibody that by virtue of its origin or source of derivation has one, two, three or four of the following: (1) is not associated with naturally associated components that accompany it in its native state, (2) is free of other proteins from the same species, (3) is expressed by a cell from a different species, and (4) does not occur in nature absent the hand of man.

In an embodiment the antibody is humanized. "Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from a hypervariable region (HVR) (or CDR) of the recipient are replaced by residues from a HVR (or CDR) of a non-human species (donor antibody) such as mouse, rat, rabbit, or nonhuman primate having the desired specificity, affinity, and/or capacity. In an embodiment, the antibody has 1, 2, 3, 4, 5, or all 6 CDR1-3 of both the heavy and light chain of the murine antibodies described herein. In a preferred embodiment, framework (FR) residues of the murine mAb are replaced with corresponding human immunoglobulin variable domain framework (FR) residues. These may be modified further in embodiments to further refine antibody performance. Furthermore, in a specific embodiment, humanized antibodies may comprise residues that are not found in the recipient antibody or in the donor antibody. In an embodiment, the humanized antibodies do not comprise residues that are not found in the recipient antibody or in the donor antibody. In general, a humanized antibody will comprise substantially all of at least one, and typically two, variable domains, in which all, or in embodiments substantially all, of the hypervariable loops correspond to those of a non-human immunoglobulin, and all, or in embodiments substantially all, of the FRs are those of a human immunoglobulin sequence. The humanized antibody optionally will also comprise at least a portion of an immunoglobulin constant region (Fc), typically that of a human immunoglobulin. See, e.g., Jones et al., Nature 321:522-525 (1986); Riechmann et al., Nature 332:323-329 (1988); Presta, Curr. Op. Struct. Biol. 2:593-596 (1992); Vaswani and Hamilton, Ann. Allergy, Asthma & Immunol. 1:105-115 (1998); Harris, Biochem. Soc. Transactions 23:1035-1038 (1995); Hurle and Gross, Curr. Op. Biotech. 5:428-433 (1994); and U.S. Pat. Nos. 6,982,321 and 7,087,409, the contents of each of which references and patents are hereby incorporated by reference in their entirety. In one embodiment where the humanized antibodies do comprise residues that are not found in the recipient antibody or in the donor antibody, the Fc regions of the antibodies are modified as described in WO 99/58572, the content of which is hereby incorporated by reference in its entirety.

Techniques to humanize a monoclonal antibody are well known and are described in, for example, U.S. Pat. Nos. 4,816,567; 5,807,715; 5,866,692; 6,331,415; 5,530,101; 5,693,761; 5,693,762; 5,585,089; and 6,180,370, the content of each of which is hereby incorporated by reference in its entirety. A number of "humanized" antibody molecules comprising an antigen-binding site derived from a non-human immunoglobulin have been described, including antibodies having rodent or modified rodent V regions and their associated complementarity determining regions (CDRs) fused to human constant domains. See, for example, Winter et al. Nature 349: 293-299 (1991), Lobuglio et al. Proc. Nat. Acad. Sci. USA 86: 4220-4224 (1989), Shaw et al. J. Immunol. 138: 4534-4538 (1987), and Brown et al. Cancer Res. 47: 3577-3583 (1987), the content of each of which is hereby incorporated by reference in its entirety. Other references describe rodent hypervariable regions or CDRs grafted into a human supporting framework region (FR) prior to fusion with an appropriate human antibody constant domain. See, for example, Riechmann et al. Nature 332: 323-327 (1988), Verhoeyen et al. Science 239: 1534-1536 (1988), and Jones et al. Nature 321: 522-525 (1986), the content of each of which is hereby incorporated by reference in its entirety. Another reference describes rodent CDRs supported by recombinantly veneered rodent framework regions—European Patent Publication No. 0519596 (incorporated by reference in its entirety). These "humanized" molecules are designed to minimize unwanted immunological response toward rodent anti-human antibody molecules which limits the duration and effectiveness of therapeutic applications of those moieties in human recipients. The antibody constant region can be engineered such that it is immunologically inert (e.g., does not trigger complement lysis). See, e.g., PCT Publication No. WO99/58572; UK Patent Application No. 9809951.8. Other methods of humanizing antibodies that may also be utilized are disclosed by Daugherty et al., Nucl. Acids Res. 19: 2471-2476 (1991) and in U.S. Pat. Nos. 6,180,377; 6,054,297; 5,997,867; 5,866,692; 6,210,671; and 6,350,861; and in PCT Publication No. WO 01/27160 (each incorporated by reference in their entirety).

Other forms of humanized antibodies have one or more, or all, CDRs (CDR L1, CDR L2, CDR L3, CDR H1, CDR H2, or CDR H3) which are altered with respect to the original antibody, which are also termed one or more CDRs "derived from" one or more CDRs from the original antibody. In an embodiment, the antibody of the invention is a humanized antibody described herein with one or more, or all, CDRs (CDR L1, CDR L2, CDR L3, CDR H1, CDR H2, or CDR H3) which are altered with respect to the original antibody. In an embodiment, the antibody of the invention is a humanized antibody described herein with none of its CDRs (CDR L1, CDR L2, CDR L3, CDR H1, CDR H2, or CDR H3) altered with respect to the original antibody.

In embodiments, the antibodies or fragments herein can be produced recombinantly, for example antibodies expressed using a recombinant expression vector transfected into a host cell, antibodies isolated from a recombinant, combinatorial human antibody library, antibodies isolated from an animal (e.g., a mouse) that is transgenic for human immunoglobulin genes.

In an embodiment, the agonist anti-ENG coreceptor antibody described herein is capable of specifically binding to or specifically binds a human ENG coreceptor. In an embodiment, the agonist anti-ENG coreceptor antibody described herein which binds the BMP9-binding region within an ectodomain of the ENG coreceptor is capable of specifically binding or specifically binds a human BMP9-binding region within an ectodomain of the ENG coreceptor. As used herein, the terms "is capable of specifically binding" or "specifically binds" refers to the property of an antibody or fragment of binding to the (specified) antigen with a dissociation constant that is <1 μM, preferably <1 nM and most preferably <10 pM. In an embodiment, the Kd of the antibody (or fragment) for ENG coreceptor is better than 10.0 nM. In an embodiment, the Kd of the antibody (or fragment) for ENG coreceptor is better than 1.0 nM. In an embodiment, the Kd of the antibody (or fragment) for ENG coreceptor is better than 0.5 nM. In an embodiment, the Kd of the antibody (or fragment) for ENG coreceptor is 0.1 nM or stronger.

The term "$K_d$", as used herein, is intended to refer to the dissociation constant of an antibody-antigen interaction. One way of determining the $K_d$ or binding affinity of antibodies to, e.g., ENG coreceptor is by measuring binding affinity of monofunctional Fab fragments of the antibody. (The affinity constant is the inverted dissociation constant). To obtain monofunctional Fab fragments, an antibody (for example, IgG) can be cleaved with papain or expressed recombinantly. The affinity of a fragment of an agonist anti-ENG coreceptor antibody can be determined, for example, by surface plasmon resonance (BIAcore3000™ surface plasmon resonance (SPR) system, BIAcore Inc., Piscataway N.J.). CM5 chips can be activated with N-ethyl-N'-(3-dimethylaminopropyl)-carbodiinide hydrochloride (EDC) and N-hydroxysuccinimide (NHS) according to the supplier's instructions. The antigen can be diluted into 10 mM sodium acetate pH 4.0 and injected over the activated chip at a concentration of 0.005 mg/mL. Using variable flow time across the individual chip channels, two ranges of antigen density can be achieved: 100-200 response units (RU) for detailed kinetic studies and 500-600 RU for screening assays. Serial dilutions (0.1-10× estimated $K_d$) of purified Fab samples are injected for 1 min at 100 microliters/min and dissociation times of up to 2 h are allowed. The concentrations of the Fab proteins are determined by ELISA and/or SDS-PAGE electrophoresis using a Fab of known concentration (as determined by amino acid analysis) as a standard. Kinetic association rates ($k_{on}$) and dissociation rates ($k_{off}$) are obtained simultaneously by fitting the data to a 1:1 Langmuir binding model (Karlsson, R. Roos, H. Fagerstam, L. Petersson, B. (1994). Methods Enzymology 6. 99-110, the content of which is hereby incorporated in its entirety) using the BIA evaluation program. Equilibrium dissociation constant ($K_d$) values are calculated as $k_{off}/k_{on}$. This protocol is suitable for use in determining binding affinity of an antibody or fragment to any antigen. Other protocols known in the art may also be used. For example, ELISA.

An epitope that "specifically binds" to an antibody or a polypeptide is a term well understood in the art, and methods to determine such specific or preferential binding are also well known in the art. A molecular entity is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an agonist antibody that specifically or preferentially binds to an ENG coreceptor is an antibody that binds this epitope with greater affinity, avidity, more readily, and/or with greater duration than it binds to other non-ENG coreceptor epitopes. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding.

The term "compete", as used herein with regard to an antibody, means that a first antibody, or an antigen-binding portion thereof, binds to an epitope in a manner sufficiently similar to the binding of a second antibody, or an antigen-binding portion thereof, such that the result of binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope or ligand, whether to the same, greater, or lesser extent, the antibodies are said to "cross-compete" with each other for binding of their respective epitope(s). Both competing and cross-competing antibodies are encompassed by the present invention. Regardless of the mechanism by which such competition or cross-competition occurs (e.g., steric hindrance, conformational change, or binding to a common epitope, or portion thereof), the skilled artisan would appreciate, based upon the teachings provided herein, that such competing and/or cross-competing antibodies are encompassed and can be useful for the methods disclosed herein.

Depending on the amino acid sequences of the constant domains of their heavy chains, antibodies (immunoglobulins) can be assigned to different classes. The antibody or fragment can be, e.g., any of an IgM, IgG, IgD, IgE or IgA antibody or fragment thereof, respectively. In an embodiment the antibody is an immunoglobulin M. In an embodiment the antibody fragment is a fragment of an immunoglobulin G. In an embodiment the antibody is an IgG1, IgG2, IgG2a, IgG2b, IgG3 or IgG4. In an embodiment the antibody comprises sequences from a human IgG1, human IgG2, human IgG2a, human IgG2b, human IgG3 or human IgG4. A combination of any of these antibody subtypes can also be used. One consideration in selecting the type of antibody to be used is the desired serum half-life of the antibody. For example, an IgG generally has a serum half-life of 23 days, IgA 6 days, IgM 5 days, IgD 3 days, and IgE 2 days. (Abbas A K, Lichtman A H, Pober J S. Cellular and Molecular Immunology, 4th edition, W.B. Saunders Co., Philadelphia, 2000, hereby incorporated by reference in its entirety).

The "variable region" or "variable domain" of an antibody refers to the amino-terminal domains of the heavy or light chain of the antibody. The variable domain of the heavy chain may be referred to as "VH." The variable domain of the light chain may be referred to as "VL." These domains are generally the most variable parts of an antibody and contain the antigen-binding sites. The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions (HVRs) (or CDRs) both in the light-chain and the heavy-chain variable domains. The more highly conserved portions of variable domains are called the framework regions (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen-binding site of antibodies (see Kabat et al., Sequences of Proteins of Immunological Interest, Fifth Edition, National Institutes of Health, Bethesda, Md. (1991)). The constant domains are not involved directly in the binding of an antibody to an antigen, but exhibit various effector functions, such as participation of the antibody in antibody-dependent cellular toxicity.

The "light chains" of antibodies (immunoglobulins) from any vertebrate species can be assigned to one of two clearly distinct types, called kappa (κ) and lambda (λ), based on the amino acid sequences of their constant domains.

"Framework" or "FR" residues are those variable domain residues other than the HVR residues as herein defined.

The term "hypervariable region" or "HVR" when used herein refers to the regions of an antibody variable domain which are hypervariable in sequence and/or form structurally defined loops. Generally, antibodies comprise six HVRs; three in the VH (H1, H2, H3) and three in the VL (L1, L2, L3). In native antibodies, H3 and L3 display the most diversity of the six HVRs, and H3 in particular is believed to play a unique role in conferring fine specificity to antibodies. See, e.g., Xu et al., Immunity 13:37-45 (2000); Johnson and Wu, in Methods in Molecular Biology 248:1-25 (Lo, ed., Human Press, Totowa, N.J., 2003). Indeed, naturally occurring camelid antibodies consisting of a heavy chain only are functional and stable in the absence of light chain. See, e.g., Hamers-Casterman et al., Nature 363:446-448 (1993); Sheriff et al., Nature Struct. Biol. 3:733-736 (1996). A number of HVR delineations are in use and are encompassed herein. The Kabat Complementarity Determining Regions (CDRs) are based on sequence variability and are the most commonly used (Kabat et al., Sequences of Proteins of Immunological Interest, 5th Ed. Public Health Service, National Institutes of Health, Bethesda, Md. (1991) hereby incorporated by reference in its entirety). There are CDRs 1, 2, and 3 for each of the heavy and light chains. Chothia refers instead to the location of the structural loops (Chothia and Lesk, J. Mol. Biol. 196:901-917 (1987)). The AbM HVRs represent a compromise between the Kabat HVRs and Chothia structural loops, and are used by Oxford Molecular's AbM antibody modeling software. The "contact" HVRs are based on an analysis of the available complex crystal structures. HVRs may comprise "extended HVRs" as follows: 24-36 or 24-34 (L1), 46-56 or 50-56 (L2) and 89-97 or 89-96 (L3) in the VL and 26-35 (H1), 50-65 or 49-65 (H2) and 93-102, 94-102, or 95-102 (H3) in the VH. The variable domain residues are numbered according to Kabat et al., supra, for each of these definitions.

The term "Fc region" herein is used to define a C-terminal region of an immunoglobulin heavy chain, including native sequence Fc regions and variant Fc regions. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The C-terminal lysine of the Fc region may be removed, for example, during production or purification of the antibody, or by recombinantly engineering the nucleic acid encoding a heavy chain of the antibody. Accordingly, an intact antibody as used herein may be an antibody with or without the otherwise C-terminal lysine.

Compositions or pharmaceutical compositions comprising the antibodies, ScFvs or fragments of antibodies disclosed herein preferably comprise stabilizers to prevent loss of activity or structural integrity of the protein due to the effects of denaturation, oxidation or aggregation over a period of time during storage and transportation prior to use. The compositions or pharmaceutical compositions can comprise one or more of any combination of salts, surfactants, pH and tonicity agents such as sugars (that can contribute to overcoming aggregation problems). Where a composition or pharmaceutical composition of the present invention is used as an injection, it is desirable to have a pH value in an approximately neutral pH range, it is also advantageous to minimize surfactant levels to avoid bubbles in the formulation which are detrimental for injection into subjects. In an embodiment, the composition or pharmaceutical composition is in liquid form and stably supports high concentrations of bioactive antibody in solution and is suitable for inhalational or parenteral administration. In an embodiment, the composition or pharmaceutical composition is suitable for intravenous, intramuscular, intraperitoneal, intradermal and/or subcutaneous injection. In an embodiment, the composition or pharmaceutical composition is in liquid form and has minimized risk of bubble formation and anaphylactoid side effects. In an embodiment, the composition or pharmaceutical composition is isotonic. In an embodiment, the composition or pharmaceutical composition has a pH or 6.8 to 7.4.

In an embodiment the ScFvs or fragments of antibodies disclosed herein are lyophilized and/or freeze dried and are reconstituted for use.

Examples of pharmaceutically acceptable carriers include, but are not limited to, phosphate buffered saline solution, sterile water (including water for injection USP), emulsions such as oil/water emulsion, and various types of wetting agents. Preferred diluents for aerosol or parenteral administration are phosphate buffered saline or normal (0.9%) saline, for example 0.9% sodium chloride solution, USP. Compositions comprising such carriers are formulated by well known conventional methods (see, for example, Remington's Pharmaceutical Sciences, 18th edition, A. Gennaro, ed., Mack Publishing Co., Easton, Pa., 1990; and Remington, The Science and Practice of Pharmacy 20th Ed. Mack Publishing, 2000, the content of each of which is hereby incorporated in its entirety). In non-limiting examples, the carriers can comprise one or more of dibasic sodium phosphate, potassium chloride, monobasic potassium phosphate, polysorbate 80 (e.g. 2-[2-[3,5-bis(2-hydroxyethoxy)oxolan-2-yl]-2-(2-hydroxyethoxy)ethoxy]ethyl (E)-octadec-9-enoate), disodium edetate dehydrate, sucrose, monobasic sodium phosphate monohydrate, and dibasic sodium phosphate dihydrate.

The antibodies, or fragments of antibodies, or compositions, or pharmaceutical compositions described herein can also be lyophilized or provided in any suitable forms including, but not limited to, injectable solutions or inhalable solutions, gel forms and tablet forms.

The term "Fc domain" herein is used to define a C-terminal region of an immunoglobulin heavy chain, including native sequence Fc regions and variant Fc regions. Although the boundaries of the Fc domain of an immunoglobulin heavy chain might vary, the human IgG heavy chain Fc domain is usually defined to stretch from an amino acid residue at position Cys226, or from Pro230, to the carboxyl-terminus thereof. The C-terminal lysine of the Fc domain may be removed, for example, by recombinantly engineering the nucleic acid encoding it. In embodiments, the antibody comprises an Fc domain. In an embodiment, the Fc domain has the same sequence or 99% or greater sequence similarity with a human IgG1 Fc domain. In an embodiment, the Fc domain has the same sequence or 99% or greater sequence similarity with a human IgG2 Fc domain. In an embodiment, the Fc domain has the same sequence or 99% or greater sequence similarity with a human IgG3 Fc domain. In an embodiment, the Fc domain has the same sequence or 99% or greater sequence similarity with a human IgG4 Fc domain. In an embodiment, the Fc domain is not mutated. In an embodiment, the Fc domain is mutated at the CH2-CH3 domain interface to increase the affinity of IgG for FcRn at acidic but not neutral pH (Dall'Acqua et al, 2006; Yeung et al, 2009). In an embodiment, the Fc domain has the same sequence as a human IgG1 Fc domain.

In embodiments, the invention encompasses modifications to the variable regions disclosed herein. For example, the invention includes antibodies comprising functionally equivalent variable regions and CDRs which do not significantly affect their properties as well as variants which have enhanced or decreased activity and/or affinity. Modification of polypeptides is routine practice in the art and need not be described in detail herein. Examples of modified polypeptides include polypeptides with conservative substitutions of amino acid residues, one or more deletions or additions of amino acids which do not significantly deleteriously change the functional activity, or which mature (enhance) the affinity of the polypeptide for its ligand, or use of chemical analogs.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to an epitope tag. Other insertional variants of the antibody molecule include the fusion to the N- or C-terminus of the antibody of an enzyme or a polypeptide which increases the half-life of the antibody in the blood circulation.

Substitution variants have at least one amino acid residue in the antibody molecule removed and a different residue inserted in its place. The sites of greatest interest for substitutional mutagenesis include the hypervariable regions, but framework alterations are also contemplated. Conservative substitutions are shown in Table 1 under the heading of "conservative substitutions." If such substitutions result in a change in biological activity, then more substantial changes, denominated "exemplary substitutions" in Table 1, or as further described below in reference to amino acid classes, may be introduced and the products screened.

TABLE 1

Amino Acid Substitutions

| Original Residue | Conservative Substitutions | Exemplary Substitutions |
|---|---|---|
| Ala (A) | Val | Val; Leu; Ile |
| Arg (R) | Lys | Lys; Gln; Asn |
| Asn (N) | Gln | Gln; His; Asp, Lys; Arg |
| Asp (D) | Glu | Glu; Asn |
| Cys (C) | Ser | Ser; Ala |
| Gln (Q) | Asn | Asn; Glu |
| Glu (E) | Asp | Asp; Gln |
| Gly (G) | Ala | Ala |
| His (H) | Arg | Asn; Gln; Lys; Arg |
| Ile (I) | Leu | Leu; Val; Met; Ala; Phe; Norleucine |
| Leu (L) | Ile | Norleucine; Ile; Val; Met; Ala; Phe |
| Lys (K) | Arg | Arg; Gln; Asn |
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |
| Tyr (Y) | Phe | Trp; Phe; Thr; Ser |
| Val (V) | Leu | Ile; Leu; Met; Phe; Ala; Norleucine |

Substantial modifications in the biological properties of the antibody are accomplished by selecting substitutions that differ significantly in their effect on maintaining (a) the structure of the polypeptide backbone in the area of the substitution, for example, as a β-sheet or helical conformation, (b) the charge or hydrophobicity of the molecule at the target site, or (c) the bulk of the side chain. Naturally occurring residues are divided into groups based on common side-chain properties:

(1) Non-polar: Norleucine, Met, Ala, Val, Leu, Ile;
(2) Polar without charge: Cys, Ser, Thr, Asn, Gln;
(3) Acidic (negatively charged): Asp, Glu;
(4) Basic (positively charged): Lys, Arg;
(5) Residues that influence chain orientation: Gly, Pro; and
(6) Aromatic: Trp, Tyr, Phe, His.

Non-conservative substitutions are made by exchanging a member of one of these classes for another class.

One type of substitution, for example, that may be made is to change one or more cysteines in the antibody, which may be chemically reactive, to another residue, such as, without limitation, alanine or serine. For example, there can be a substitution of a non-canonical cysteine. The substitution can be made in a CDR or framework region of a variable domain or in the constant region of an antibody. In some embodiments, the cysteine is canonical. Any cysteine residue not involved in maintaining the proper conformation of the antibody also may be substituted, generally with serine, to improve the oxidative stability of the molecule and prevent aberrant cross-linking. Conversely, cysteine bond(s) may be added to the antibody to improve its stability, particularly where the antibody is an antibody fragment such as an Fv fragment.

The antibodies may also be modified, e.g., in the variable domains of the heavy and/or light chains, e.g., to alter a binding property of the antibody. Changes in the variable region can alter binding affinity and/or specificity. In some embodiments, no more than one to five conservative amino acid substitutions are made within a CDR domain. In other embodiments, no more than one to three conservative amino acid substitutions are made within a CDR domain. For example, a mutation may be made in one or more of the CDR regions to increase or decrease the $K_D$ of the agonist anti-ENG coreceptor, to increase or decrease $k_{off}$, or to alter the binding specificity of the antibody. Techniques in site-directed mutagenesis are well-known in the art.

A modification or mutation may also be made in a framework region or constant region to increase the half-life of an agonist anti-ENG coreceptor antibody. See, e.g., PCT Publication No. WO 00/09560. A mutation in a framework region or constant region can also be made to alter the immunogenicity of the antibody, to provide a site for covalent or non-covalent binding to another molecule, or to alter such properties as complement fixation, FcR binding and antibody-dependent cell-mediated cytotoxicity. According to the invention, a single antibody may have mutations in any one or more of the CDRs or framework regions of the variable domain or in the constant region.

In an embodiment, an antibody described herein is recombinantly produced. In an embodiment, the antibody produced in the eukaryotic expression system comprises glycosylation at a residue on the Fc portion corresponding to Asn297.

In an embodiment the composition or pharmaceutical composition comprising the antibody, or antigen-binding fragment thereof, described herein is substantially pure with regard to the antibody, or antigen-binding fragment thereof. A composition or pharmaceutical composition comprising the antibody, or antigen-binding fragment thereof, described herein is "substantially pure" with regard to the antibody or fragment when at least 60% to 75% of a sample of the composition or pharmaceutical composition exhibits a single species of the antibody, or antigen-binding fragment thereof. A substantially pure composition or pharmaceutical composition comprising the antibody, or antigen-binding fragment thereof, described herein can comprise, in the portion thereof which is the antibody, or antigen-binding fragment, 60%, 70%, 80% or 90% of the antibody, or antigen-binding fragment, of the single species, more usually about 95%, and preferably over 99%. Purity or homogeneity may be tested by a number of means well known in the art, such as polyacrylamide gel electrophoresis or HPLC.

Human ENG co-receptor encoding sequences are known in the art. For example, NCBI Reference Sequence: NG_009551.1; Ensembl Gene ID: ENG ENSG00000106991.

In regard to BMP9, both BMP9 and BMP10 are circulating ligands with comparable and high affinity for ENG binding. Both ligands induce expression of similar downstream target genes, suggesting the presence of a strong functional redundancy between BMP9 and BMP10. Although only the structural interaction between BMP9 and ENG has been resolved so far, it is highly likely that BMP9 and BMP10, knowing their sequence and functional similarities, should bind to the same domain on ENG to activate the receptor, see Refs PMID: 31828546, 28564608. Therefore, it is predicted that an agonist mAb binding ENG will mimic BMP9 and BMP10 signaling.

A host cell comprising one or more of the nucleic acids described herein.

An antibody or fragment thereof described herein linked or conjugated to a therapeutic agent.

In embodiments, the therapeutic agent is a cytotoxic drug, a radioactive isotope, an immunomodulator, or a second antibody.

A pharmaceutical composition comprising an effective amount of the isolated antibody or antibody fragment as described herein, and a pharmaceutically acceptable carrier or excipient, is provided.

In embodiments, the subject is a mammal.

In embodiments, the mammal is a human.

"And/or" as used herein, for example, with option A and/or option B, encompasses the separate embodiments of (i) option A, (ii) option B, and (iii) option A plus option B.

All combinations of the various elements described herein are within the scope of the invention unless otherwise indicated herein or otherwise clearly contradicted by context.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

Pharmaceutically active: The term "pharmaceutically active" as used herein refers to the beneficial biological activity of a substance on living matter and, in particular, on cells and tissues of the human body. A "pharmaceutically active agent" or "drug" is a substance that is pharmaceutically active and a "pharmaceutically active ingredient" (API) is the pharmaceutically active substance in a drug.

Pharmaceutically acceptable: The term "pharmaceutically acceptable" as used herein means approved by a regulatory agency of the Federal or a state government or listed in the U.S. Pharmacopoeia, other generally recognized pharmacopoeia in addition to other formulations that are safe for use in animals, and more particularly in humans and/or non-human mammals.

Pharmaceutically acceptable salt: The term "pharmaceutically acceptable salt" as used herein refers to acid addition salts or base addition salts of the compounds, such as the multi-drug conjugates, in the present disclosure. A pharmaceutically acceptable salt is any salt which retains the activity of the present antibody or fragment. Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenyl acetates, phenylpropionates, phenylbutyrates, citrates, lactates, [gamma]-hydroxybutyrates, glycolates, tartrates, and mandelates.

Pharmaceutically acceptable carrier: The term "pharmaceutically acceptable carrier" as used herein refers to an excipient, diluent, preservative, solubilizer, emulsifier, adjuvant, and/or vehicle with which the present antibody or fragment is administered. Such carriers may be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. Antibacterial agents such as benzyl alcohol or methyl parabens; antioxidants such as ascorbic acid or sodium bisulfate; chelating agents such as ethylenediaminetetraacetic acid; and agents for the adjustment of tonicity such as sodium chloride or dextrose may also be a carrier. Methods for producing compositions in combination with carriers are known to those of skill in the art. In some embodiments, the language "pharmaceutically acceptable carrier" is intended to include any and all solvents, dispersion media, coatings, isotonic and absorption delaying agents, and the like, compatible with pharmaceutical administration. The use of such media and agents for pharmaceutically active substances is well known in the art. See, e.g., Remington, The Science and Practice of Pharmacy. 20$^{th}$ ed., (Lippincott, Williams & Wilkins 2003). Except insofar as any conventional media or agent is incompatible with the active compound, such use in the compositions is contemplated.

"Treating" or "treatment" or "alleviation" refers to therapeutic treatment wherein the object is to slow down (lessen) if not cure the targeted pathologic condition or disorder or prevent recurrence of the condition. A subject is successfully "treated" if, after receiving a therapeutic amount of a therapeutic agent, the subject shows observable and/or measurable reduction in or absence of one or more signs and symptoms of the particular disease. Reduction of the signs or symptoms of a disease may also be felt by the patient. A patient is also considered treated if the patient experiences stable disease. In some embodiments, treatment with a therapeutic agent is effective to result in the patients being disease-free 3 months after treatment, preferably 6 months, more preferably one year, even more preferably 2 or more years post treatment. These parameters for assessing successful treatment and improvement in the disease are readily measurable by routine procedures familiar to a physician of appropriate skill in the art.

As used herein, "preventative" treatment is meant to indicate a postponement of development of a disease, a symptom of a disease, or medical condition, suppressing symptoms that may appear, or reducing the risk of developing or recurrence of a disease or symptom. "Curative" treatment includes reducing the severity of or suppressing the worsening of an existing disease, symptom, or condition.

It is understood that aspects and embodiments of the invention described herein include "consisting" and/or "consisting essentially of" aspects and embodiments.

Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range. Thus, "85% or more" identity to something shall mean all percentage identities from 85% up to 100%.

As used herein, a subject, unless otherwise indicated, refers to an animal, a non-human mammal or a human. As used herein, "animals" include a pet, a farm animal, an economic animal, a sport animal and an experimental animal, such as a cat, a dog, a horse, a cow, an ox, a pig, a donkey, a sheep, a lamb, a goat, a mouse, a rabbit, a chicken, a duck, a goose, a primate, including a monkey and a chimpanzee.

Other objects, advantages and features of the present invention will become apparent from the following specification taken in conjunction with the accompanying drawings.

This invention may be better understood from the Experimental Details, which follow.

EXPERIMENTAL DETAILS

By targeting a BMP9 binding sequence of endoglin, an antibody has been created which is able to directly and efficiently activate endoglin signaling. This endoglin agonist antibody serves as a BMP9 mimetic that directly activates endoglin (ENG) and rescues endoglin functions in HHT and PAH.

An ENG agonist IgM mAb, "A18-384" or "A18", has been generated in mice. Using a combination of ammonium sulfate precipitation and IgM purification columns, small quantities of ENG mAb A18-384 were successfully purified (purification yield ~80%). These purification experiments were performed with hybridoma-conditioned medium containing FBS. It was also confirmed that the use of a serum-free hybridoma medium did not significantly affect ENG mAb titer.

Figure 2:
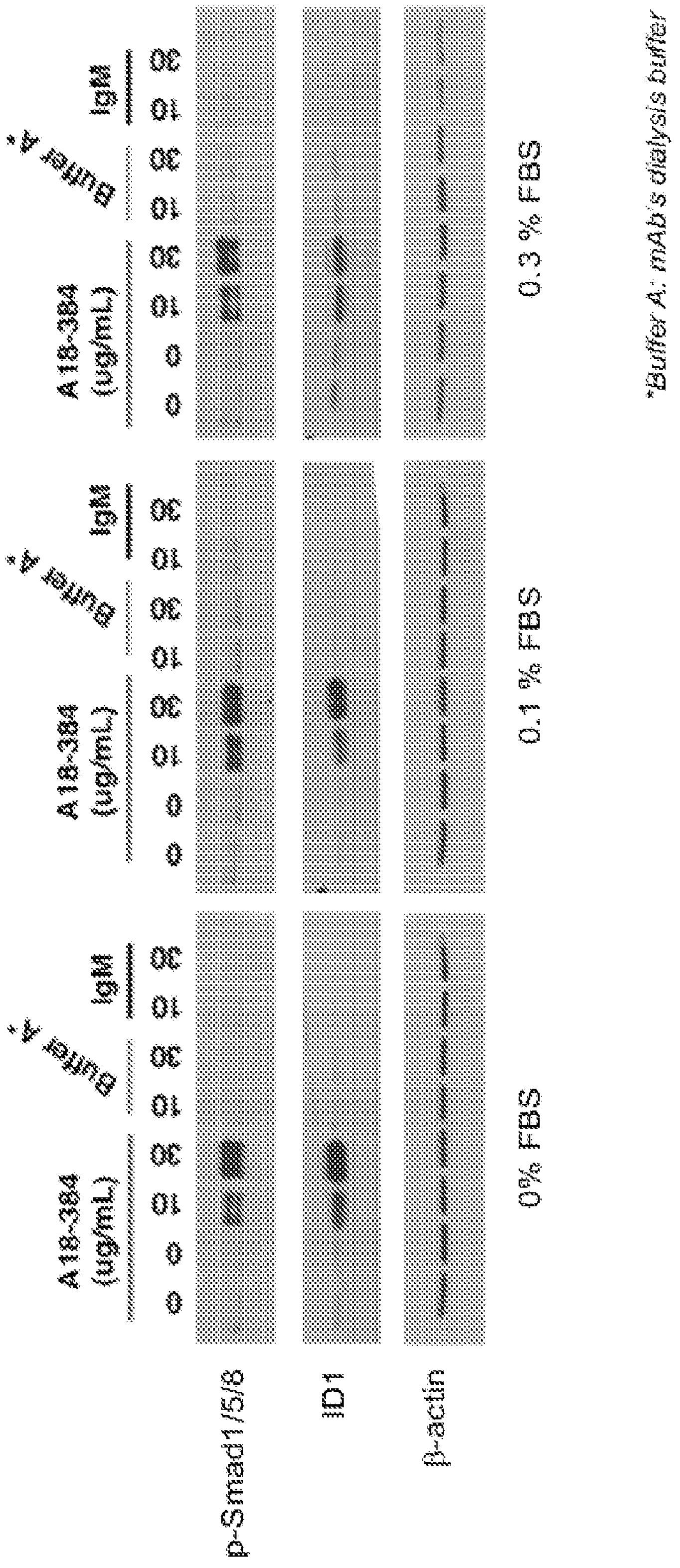
FIG. 2: Identification of an anti-ENG agonist mAb and its action effecting SMAD/1/5/8 activity, i.e., SMAD/1/5/8 phosphorylation and ID1 expression.

The antibody was successfully tested on MS1 endothelial cells for ENG-SMAD1/5/8 signaling activation (see FIG. 2).

The agonist mAb A18-384 is also tested on primary endothelial cells isolated from lungs and livers of wild-type C57BL/6 mice. In addition, the agonist mAb A18-384 is injected in wild-type C57BL/6 mice to assess its SMAD1/5/8 signaling activating properties and its stability in the blood circulation. Intraperitoneal injections of doses of up to 10 mg/kg are used. Endothelial SMAD1/5/8 signaling activation is assessed in the lungs and liver by immunohistochemistry and Western blotting techniques and by measuring phospho-SMAD1/5/8 and ID1 (inhibitor of DNA binding protein 1) levels, as before [9,10].

The in vivo efficacy of the ENG agonist mAb A18-384 in rescuing endothelial SMAD1/5/8 signaling and in preventing and reversing AVM pathology in HHT mice is tested. The HHT model used is BMP9/10-immunoblocked mice, which develop retinal AVMs, but also robust vascular pathology in the liver, lungs, and mucosa, as well as pronounced anemia [9,10,15]. This model is of particular interest because neutralization of the BMP9/10 ligands leads to a clear inhibition of ALK1-ENG receptor function [9]. An ENG agonist mAb such as A18-384 that can bypass ligand neutralization and activate ENG will prevent the resulting SMAD1/5/8 inhibition-mediated pathogenesis.

The in vivo efficacy of the ENG agonist mAb A18-384 in blocking PAH pathology in rodents is tested on the monocrotaline-induced PH rodent model. It is determined whether ENG agonist mAb A18-384 treatment prevents right ventricular systolic pressure (RVSP), prevents RV hypertrophy, pulmonary arterial muscularization, and endothelial cell apoptosis.

Human cell testing for HHT and PAH treatment can be effected using the mAb(s) in human endothelial cell cultures, including in HHT-derived blood outgrowth endothelial cells (BOECs) for its efficacy in activating ENG-SMAD1/5/8 signaling. BOECs were isolated from both HHT1 and HHT2 patients [9,10].

CDR sequencing from the A18 hybridoma revealed heavy chain CDR1: GFTFNTYA (SEQ ID NO:3); CDR2: IRSKSSNYAT (SEQ ID NO:4) and CDR3: VRDRTGSWFAY (SEQ ID NO:5). Similarly, CDR sequencing from the A18 hybridoma revealed light chain CDR1: QDIGSS (SEQ ID NO:6); CDR2: ATS (SEQ ID NO:7); and CDR3: LQYASSPYT (SEQ ID NO:8). The variable heavy chain had the sequence SEQ ID NO:17. Full heavy chain, signal, variable and constant, was encoded by SEQ ID NO:10, and had the sequence SEQ ID NO:11. The variable light chain had the sequence SEQ ID NO:18. Full light chain, signal, variable and constant, was encoded by SEQ ID NO:12, and had the sequence SEQ ID NO:13.

Sequencing was performed by:

1. Total RNA extraction from B cells
2. mRNA denaturing
3. cDNA synthesis
4. 5' RACE (Rapid Amplification of cDNA Ends) reaction
5. PCR result analysis
6. Cloning PCR positive bands
7. Plasmid miniprep
8. Sequencing 10 clones in total per sample
9. CDR analysis using DNA sequencing data (CDR regions were defined using IMGT/V-QUEST, world wide web at imgt.org).

Recombinant A18 scFv-Fc: CDR sequences were used to generate recombinant antibodies carrying the native variable heavy (VH) chain and variable light (VL) chain. Different combinations of VH chain, VL chain, and linkers (15 amino acids, 15aa; or 20 aa) fused to human IgG1-Fc (Fc) were generated:

LH15: VL-15aa-VH-Fc;
HL15: VH-15aa-VL-Fc;
LH20: VL-20aa-VH-Fc; and
HL20: VH-20aa-VL-Fc.

The ScFv were made by subcloning into pFuse vector (Zoecin resistance, see world wide web at invivogen.com/pfuse-higg1-fc). The sequences for each of these constructs are set forth above. All constructs showed activity, but LH15 (VL-15aa-VH-Fc) showed the strongest activity when tested by ELISA (~1:1000 titer against the original epitope peptide (SEQ ID NO:1) used for immunization).

Figure 3:
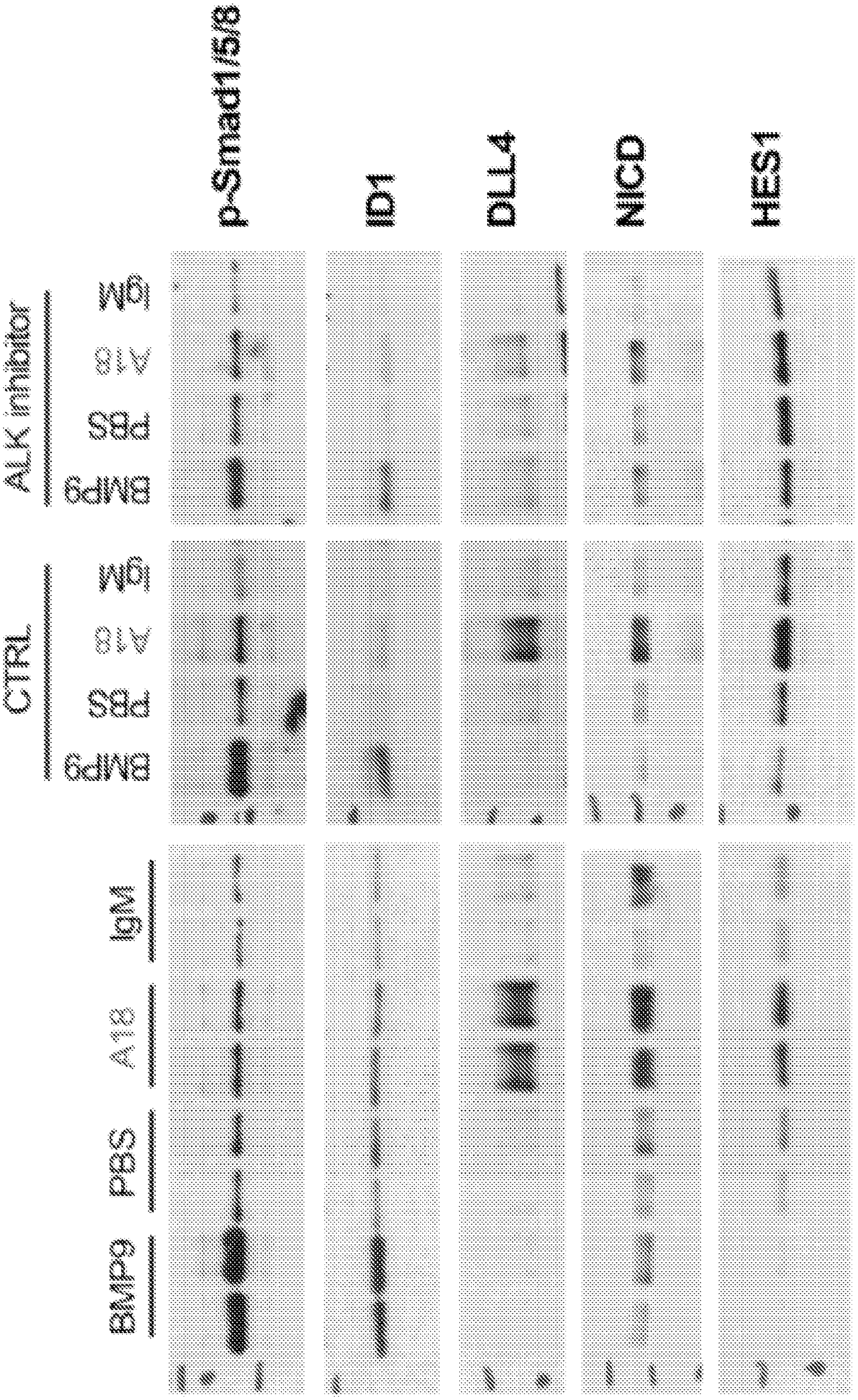
FIG. 3: A18 mAb activates Notch signaling in endothelial MS1 cells. MS1 cells were treated with BMP9, PBS (buffer only, negative control), A18, or IgM (non-specific IgM, negative control), in the absence (CTRL, middle panels) or presence of ALK inhibitor (LDN-193189, right panels). Cell homogenates were then analyzed by Western blotting against the indicated proteins. Note the robust elevation of Notch ligand, DLL4, Notch intracellular domain, NICD, and Notch transcriptional target, HES1, upon A18 treatment. Note also the blocking effect of the ALK inhibitor (right panels) on the Notch signaling activation properties of A18. These data show that anti-ENG mAb A18 activates Notch signaling and that this effect requires ALK1/ENG.

Notch activation: An anti-endoglin coreceptor agonist antibody as described herein, A18, could also robustly activate Notch signaling, via a mechanism that requires the endoglin/ALK1 receptor complex. As show in FIG. 3, the A18 mAb activates Notch signaling in endothelial MS1 cells. MS1 cells were treated with BMP9, PBS (buffer only, negative control), A18, or IgM (non-specific IgM, negative control), in the absence (CTRL, middle panels) or presence of ALK inhibitor (LDN-193189, right panels). Cell homogenates were then analyzed by Western blotting against the indicated proteins. Note the robust elevation of Notch ligand, DLL4, Notch intracellular domain, NICD, and Notch transcriptional target, HES1, upon A18 treatment. Note also the blocking effect of the ALK inhibitor (right panels) on the Notch signaling activation properties of A18. These data show that anti-ENG mAb A18 activates Notch signaling and that this effect requires ALK1/ENG.

Notch is critically involved in tissue development and homeostasis, and its deregulation controls the pathogenesis of multiple diseases, including several cancer types. In HHT, strong evidence suggests that Notch inhibition is involved in arteriovenous malformation (AVM) development, a cardinal feature of HHT vascular pathology. Experiments showed that A18 mAb is a potent Notch signaling activator.

Since Notch loss-of-function has been associated with several cancer types, including head and neck squamous cell carcinoma (HNSCC) or squamous cancer of the skin, lung, and esophagus, increasing Notch signaling is considered therapeutic in these cancer types. Interestingly, although endoglin is preferentially expressed in endothelial cells and some stem cells, its expression is increased in squamous cell carcinoma.

DISCUSSION

At least 85% of HHT patients carry disease-causing loss-of-function mutations in the genes ENG (encoding endoglin, ENG) or ACVRL1 (encoding activin receptor-like kinase 1, ALK1), which define the two disease subtypes: HHT1 (OMIM #187300) and HHT2 (#600376), respectively [1,2]. ALK1 and ENG are members of the transforming growth factor-β signaling superfamily and physically and functionally interact in the same signal transduction axis [3]. The cell surface receptor complex composed of the co-receptor ENG, the endothelial BMP type I receptor ALK1, and a BMP type II receptor (e.g., BMPR2) is activated by binding of the circulating ligands BMP9 and BMP10 [4-6]. Loss-of-function mutations in BMPR2 cause familial PAH, which can be observed in HHT patients [7], further supporting the notion that ALK1, ENG, and BMPR2 functionally interact. ALK1-ENG-BMPR2 receptor activation leads to phosphorylation of the signal transducers SMAD1, SMAD5 and SMAD8 to trigger the formation of SMAD1/5/8-SMAD4 complexes that translocate into the nucleus to control specific gene expression programs [8]. Therefore, interventions that could activate ALK1-ENG-BMPR2 receptor function have therapeutic potential in both HHT and PAH by correcting endothelial SMAD1/5/8 signaling inhibition and the associated vascular pathology.

Pharmacological enhancement of ALK1 signaling has been actively explored, including by our laboratory, and several FDA-approved drugs have shown encouraging effects in HHT mouse models [9-11]. Targeting of BMPR2 using exogenous BMP9 administration has also been investigated and demonstrated efficacy in treating PAH models [12]. These approaches, although of great interest in the absence of any other therapeutic options, suffer from their relative lack of specificity and thus might lead to possible side effects, especially in an already fragile population. In this context, it was sought to determine whether selective activation of ENG, using an agonistic anti-ENG mAb, could be achieved to overcome ENG loss-of-function in both HHT and PAH. We generated an mAb with BMP9-binding mimetic properties. This mAb (given the designation "A18-384") successfully activated ENG receptor activity and SMAD1/5/8 signaling in mouse endothelial MS1 cells, an ideal cell culture system for the analysis of ENG-SMAD1/5/8 signaling [13].

Interestingly, an anti-endoglin coreceptor agonist antibody as described herein, A18, could also robustly activate Notch signaling, via a mechanism that requires the endoglin/ALK1 receptor complex. Notch is critically involved in tissue development and homeostasis, and its deregulation controls the pathogenesis of multiple diseases, including several cancer types. Since experiments showed that treatment of endothelial MS1 cells with A18 led to a strong increase of the Notch ligand Dll4 and the generation of the Notch activated fragment NICD, and since Notch loss-of-function has been associated with several cancer types, including head and neck squamous cell carcinoma (HNSCC) or squamous cancer of the skin, lung, and esophagus, increasing Notch signaling can be considered therapeutic in these cancer types.

REFERENCES

McAllister K A, Grogg K M, Johnson D W, Gallione C J, Baldwin M A, Jackson C E, Helmbold E A, Markel D S, McKinnon W C, Murrell J, et al. (1994) Endoglin, a TGF-beta binding protein of endothelial cells, is the gene for hereditary haemorrhagic telangiectasia type 1. *Nat Genet* 8: 345-351.

2. Johnson D W, Berg J N, Baldwin M A, Gallione C J, Marondel I, Yoon S J, Stenzel T T, Speer M, Pericak- Vance M A, Diamond A, et al. (1996) Mutations in the activin receptor-like kinase 1 gene in hereditary haemorrhagic telangiectasia type 2. *Nat Genet* 13: 189-195.
3. Cai J, Pardali E, Sanchez-Duffhues G, ten Dijke P (2012) BMP signaling in vascular diseases. *FEBS Lett* 586: 1993-2002.
4. Goumans M-J, Zwijsen A, Ten Dijke P, Bailly S (2018) Bone Morphogenetic Proteins in Vascular Homeostasis and Disease. *Cold Spring Harb Perspect Biol* 10.: a031989.
5. Seki T, Yun J, Oh S P (2003) Arterial endothelium-specific activin receptor-like kinase 1 expression suggests its role in arterialization and vascular remodeling. *Circ Res* 93: 682-689.
6. Saito T, Bokhove M, Croci R, Zamora-Caballero S, Han L, Letarte M, de Sanctis D, Jovine L (2017) Structural Basis of the Human Endoglin-BMP9 Interaction: Insights into BMP Signaling and HHT1. *Cell Rep* 19: 1917-1928.
7. Newman J H, Trembath R C, Morse J A, Grunig E, Loyd J E, Adnot S, Coccolo F, Ventura C, Phillips J A 3rd, Knowles J A, et al. (2004) Genetic basis of pulmonary arterial hypertension: current understanding and future directions, *J Am Coll Cardiol* 43: 33S-39S.
8. Massagué J (2012) TGFβ signalling in context. *Nat Rev Mol Cell Biol* 13: 616-630.
9. Ruiz S, Chandakkar P, Zhao H, Papoin J, Chatterjee P K, Christen E, Metz C N, Blanc L, Campagne F, Marambaud P (2017) Tacrolimus rescues the signaling and gene expression signature of endothelial ALK1 loss-of-function and improves HHT vascular pathology. *Hum Mol Genet* 26: 4786-4798.
10. Ruiz S, Zhao H, Chandakkar P, Papoin J, Choi H, Nomura-Kitabayashi A, Patel R, Gillen M, Diao L, Chatterjee P K, et al. (2019) Correcting SMAD1/5/8, mTOR, and VEGFR2 treats pathology in hereditary hemorrhagic telangiectasia models. *J Clin Invest.* 2020 Feb. 3; 130(2): 942-957.
11. Kim Y H, Kim M-J, Choe S-W, Sprecher D, Lee Y J, P Oh S (2017) Selective effects of oral antiangiogenic tyrosine kinase inhibitors on an animal model of hereditary hemorrhagic telangiectasia. *J Thromb Haemost* 15: 1095-1102.
12. Long L, Ormiston M L, Yang X, Southwood M, Gräf S, Machado R D, Mueller M, Kinzel B, Yung L M, Wilkinson J M, et al. (2015) Selective enhancement of endothelial BMPR-II with BMP9 reverses pulmonary arterial hypertension. *Nat Med* 21: 777-785.
13. Nolan-Stevaux O, Zhong W, Culp S, Shaffer K, Hoover J, Wickramasinghe D, Ruefli-Brasse A (2012) Endoglin requirement for BMP9 signaling in endothelial cells reveals new mechanism of action for selective anti-endoglin antibodies. *PLoS One* 7: e50920.
14. Vitale F, Giliberto L, Ruiz S, Steslow K, Marambaud P, d'Abramo C (2018) Anti-tau conformational scFv MC1 antibody efficiently reduces pathological tau species in adult JNPL3 mice. *Acta Neuropathol Commun* 6: 82.
15. Ruiz S, Zhao H, Chandakkar P, Chatterjee P K, Papoin J, Blanc L, Metz C N, Campagne F, Marambaud P (2016) A mouse model of hereditary hemorrhagic telangiectasia generated by transmammary-delivered immunoblocking of BMP9 and BMP10. *Sci Rep* 5: 37366.

What is claimed is:

1. An isolated monoclonal antibody which binds to a human endoglin coreceptor, or an antigen-binding fragment of the monoclonal antibody, comprising a heavy chain variable region comprising:

GFTFNTYA; (SEQ ID NO: 3)

IRSKSSNYAT; (SEQ ID NO: 4)
and

VRDRTGSWFAY; (SEQ ID NO: 5)

and a light chain variable region comprising:

QDIGSS; (SEQ ID NO: 6)

ATS; (SEQ ID NO: 7)
and

LQYASSPYT. (SEQ ID NO: 8)

2. The isolated monoclonal antibody, or antigen-binding fragment thereof, of claim 1, which is agonistic at a human endoglin coreceptor.

3. An isolated ScFv encoded by the nucleotide sequence set forth in one of SEQ ID NOs:13, 14, 15 or 16, or an isolated ScFv comprising SEQ ID NO:17 and SEQ ID NO:18.

4. The isolated monoclonal antibody or fragment thereof of claim 1, wherein framework regions of the light chain and/or the heavy chain are human framework regions, or have 85% or more identity thereto.

5. The isolated monoclonal antibody or fragment thereof of claim 4, wherein framework regions of the light chain and/or the heavy chain are human framework regions.

6. The monoclonal antibody of claim 1.

7. The antigen-binding fragment of the monoclonal antibody of claim 1.

8. The monoclonal antibody of claim 1, wherein the monoclonal antibody is an IgM.

9. The isolated monoclonal antibody or antigen-binding fragment thereof of claim 1, which comprises a human Fc region.

10. A composition comprising an isolated nucleic acid encoding a heavy chain variable region of an antibody which comprises:

GFTFNTYA (SEQ ID NO:3);

IRSKSSNYAT (SEQ ID NO:4); and

VRDRTGSWFAY (SEQ ID NO:5);

and an isolated nucleic acid encoding a light chain variable region of the antibody which comprises:

QDIGSS (SEQ ID NO:6);
ATS (SEQ ID NO:7); and
LQYASSPYT (SEQ ID NO:8)

wherein the antibody binds human endoglin coreceptor.

11. The isolated monoclonal antibody or fragment thereof according to claim 1, linked or conjugated to a therapeutic agent, an imaging agent, or a detectable marker.

12. The isolated monoclonal antibody or fragment thereof according to claim 11, wherein the therapeutic agent is a cytotoxic drug, a radioactive isotope, an immunomodulator, or a second antibody.

13. A pharmaceutical composition comprising an amount of the antibody or antigen-binding fragment of claim 1, and a pharmaceutically acceptable carrier.

14. A method of treating hereditary hemorrhagic telangiectasia or preventing one or more symptoms of hereditary hemorrhagic telangiectasia in a subject comprising administering to the subject an amount of the isolated monoclonal antibody or fragment thereof of claim 1 effective to treat or prevent one or more symptoms of hereditary hemorrhagic telangiectasia.

15. A method of treating pulmonary arterial hypertension or preventing one or more symptoms of pulmonary arterial hypertension in a subject comprising administering to the subject an amount of the isolated monoclonal antibody or fragment thereof of claim 1 effective to treat or prevent one or more symptoms of pulmonary arterial hypertension.

16. A method of activating activin receptor-like kinase 1 (ALK1) signaling or ALK1-ENG-BMPR2 receptor activation by an ENG co-receptor comprising contacting the ENG co-receptor with an amount of the isolated monoclonal antibody or fragment thereof of claim 1.

17. A method of effecting phosphorylation of at least one of endothelial SMAD1, SMAD5 and SMAD8 associated with activation of an ENG co-receptor comprising contacting the ENG co-receptor with an amount of the isolated monoclonal antibody or fragment thereof of claim 1.

18. A method of treating a cancer in a subject comprising administering to the subject an amount of the isolated monoclonal antibody or fragment thereof of claim 1 effective to treat the cancer in the subject, wherein cells of the cancer express endoglin.

19. The method of claim 18, wherein the cancer is head and neck squamous cell carcinoma (HNSCC), squamous cancer of the skin, squamous cancer of the lung, or squamous cancer of the esophagus.

20. An isolated monoclonal antibody which binds to a human endoglin coreceptor, or an antigen-binding fragment of the monoclonal antibody, comprising each CDR present in SEQ ID NO:17 and SEQ ID NO:18, wherein the antibody or antigen-binding fragment comprises a heavy chain variable region comprising:

```
                                        (SEQ ID NO: 3)
GFTFNTYA;
                                        (SEQ ID NO: 4)
IRSKSSNYAT;
and
                                        (SEQ ID NO: 5)
VRDRTGSWFAY;
```

and a light chain variable region comprising:

```
                                        (SEQ ID NO: 6)
QDIGSS;
                                        (SEQ ID NO: 7)
ATS;
and
                                        (SEQ ID NO: 8)
LQYASSPYT.
```

* * * * *

SEQUENCE LISTING

```
<160> NUMBER OF SEQ ID NOS: 18

<210> SEQ ID NO 1
<211> LENGTH: 11
<212> TYPE: PRT
<213> ORGANISM: HOMO SAPIENS

<400> SEQUENCE: 1

Thr Thr Gly Glu Tyr Ser Phe Lys Ile Phe Pro
1               5                   10


<210> SEQ ID NO 2
<211> LENGTH: 11
<212> TYPE: PRT
<213> ORGANISM: HOMO SAPIENS

<400> SEQUENCE: 2

Thr Thr Gly Glu Tyr Ser Val Lys Ile Phe Pro
1               5                   10


<210> SEQ ID NO 3
<211> LENGTH: 8
<212> TYPE: PRT
<213> ORGANISM: MURINE SP.

<400> SEQUENCE: 3

Gly Phe Thr Phe Asn Thr Tyr Ala
1               5


<210> SEQ ID NO 4
<211> LENGTH: 10
<212> TYPE: PRT
<213> ORGANISM: MURINE SP.
```

<400> SEQUENCE: 4

Ile Arg Ser Lys Ser Ser Asn Tyr Ala Thr
1 5 10

<210> SEQ ID NO 5
<211> LENGTH: 11
<212> TYPE: PRT
<213> ORGANISM: MURINE SP.

<400> SEQUENCE: 5

Val Arg Asp Arg Thr Gly Ser Trp Phe Ala Tyr
1 5 10

<210> SEQ ID NO 6
<211> LENGTH: 6
<212> TYPE: PRT
<213> ORGANISM: MURINE SP.

<400> SEQUENCE: 6

Gln Asp Ile Gly Ser Ser
1 5

<210> SEQ ID NO 7
<211> LENGTH: 3
<212> TYPE: PRT
<213> ORGANISM: MURINE SP.

<400> SEQUENCE: 7

Ala Thr Ser
1

<210> SEQ ID NO 8
<211> LENGTH: 9
<212> TYPE: PRT
<213> ORGANISM: MURINE SP.

<400> SEQUENCE: 8

Leu Gln Tyr Ala Ser Ser Pro Tyr Thr
1 5

<210> SEQ ID NO 9
<211> LENGTH: 218
<212> TYPE: PRT
<213> ORGANISM: MURINE SP.

<400> SEQUENCE: 9

Met Val Leu Gly Leu Lys Trp Val Phe Phe Val Val Phe Tyr Gln Gly
1 5 10 15

Val His Cys Glu Val Gln Leu Val Glu Ser Gly Gly Gly Leu Val Gln
20 25 30

Pro Lys Gly Ser Leu Lys Leu Ser Cys Ala Ala Ser Gly Phe Thr Phe
35 40 45

Asn Thr Tyr Ala Met His Trp Val Arg Gln Ala Pro Gly Lys Gly Leu
50 55 60

Glu Trp Val Ala Arg Ile Arg Ser Lys Ser Ser Asn Tyr Ala Thr Tyr
65 70 75 80

Tyr Ala Asp Ser Val Lys Asp Arg Phe Thr Ile Ser Arg Asp Asp Ser
85 90 95

Gln Ser Met Leu Tyr Leu Gln Met Asn Asn Leu Lys Thr Glu Asp Thr
100 105 110

```
Ala Met Tyr Tyr Cys Val Arg Asp Arg Thr Gly Ser Trp Phe Ala Tyr
        115                 120                 125

Trp Gly Gln Gly Thr Leu Val Thr Val Ser Ala Glu Ser Gln Ser Phe
    130                 135                 140

Pro Asn Val Phe Pro Leu Val Ser Cys Glu Ser Pro Leu Ser Asp Lys
145                 150                 155                 160

Asn Leu Val Ala Met Gly Cys Leu Ala Arg Asp Phe Leu Pro Ser Thr
                165                 170                 175

Ile Ser Phe Thr Trp Asn Tyr Gln Asn Asn Thr Glu Val Ile Gln Ser
            180                 185                 190

Ile Arg Thr Phe Pro Thr Leu Arg Thr Gly Gly Lys Tyr Leu Ala Thr
        195                 200                 205

Ser Gln Val Leu Leu Ser Pro Lys Ser Ile
    210                 215


<210> SEQ ID NO 10
<211> LENGTH: 654
<212> TYPE: DNA
<213> ORGANISM: MURINE SP.

<400> SEQUENCE: 10

atggtgttgg ggcttaagtg ggttttcttt gttgtttttt atcaaggtgt gcattgtgag     60

gtgcagcttg ttgagtctgg tggaggattg gtgcagccta aaggatcatt gaaactctca    120

tgtgccgcct ctggtttcac cttcaatacc tatgccatgc actgggtccg ccaggctcca    180

ggaaagggtt tggaatgggt tgctcgcata agaagtaaaa gtagtaatta tgcaacatat    240

tatgccgatt cagtgaaaga cagattcacc atctccagag atgattcaca aagcatgctc    300

tatctgcaaa tgaacaacct gaaaactgag gacacagcca tgtattactg tgtgagagat    360

agaactgggt cctggtttgc ttactggggc caagggactc tggtcactgt ctctgcagag    420

agtcagtcct tcccaaatgt cttcccccctc gtctcctgcg agagcccccct gtctgataag    480

aatctggtgg ccatgggctg cctggcccgg gacttcctgc ccagcaccat ttccttcacc    540

tggaactacc agaacaacac tgaagtcatc cagagtatca gaaccttccc aacactgagg    600

acagggggca agtacctagc cacctcgcag gtcttgctgt ctcccaagag catc          654


<210> SEQ ID NO 11
<211> LENGTH: 203
<212> TYPE: PRT
<213> ORGANISM: MURINE SP.

<400> SEQUENCE: 11

Met Arg Ala Pro Ala Gln Ile Phe Gly Phe Leu Leu Leu Leu Phe Pro
1               5                   10                  15

Gly Thr Arg Cys Asp Ile Gln Met Thr Gln Ser Pro Ser Ser Leu Ser
            20                  25                  30

Ala Ser Leu Gly Glu Arg Val Ser Leu Thr Cys Arg Ala Ser Gln Asp
        35                  40                  45

Ile Gly Ser Ser Leu Asn Trp Leu Gln Gln Glu Pro Asp Gly Thr Ile
    50                  55                  60

Lys Arg Leu Ile Tyr Ala Thr Ser Ser Leu Asp Ser Gly Val Pro Lys
65                  70                  75                  80

Arg Phe Ser Gly Ser Arg Ser Gly Ser Asp Tyr Ser Leu Thr Ile Ser
                85                  90                  95

Ser Leu Glu Ser Glu Asp Phe Val Asp Tyr Tyr Cys Leu Gln Tyr Ala
            100                 105                 110
```

```
Ser Ser Pro Tyr Thr Phe Gly Gly Gly Thr Lys Leu Glu Ile Lys Arg
        115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys
        195                 200


<210> SEQ ID NO 12
<211> LENGTH: 609
<212> TYPE: DNA
<213> ORGANISM: MURINE SP.

<400> SEQUENCE: 12

atgagggctc ctgcacaaat ttttggcttc ttgttgctct tgtttccagg taccagatgt      60

gacatccaga tgacccagtc tccatcctcc ttatctgcct ctctgggaga aagagtcagt     120

ctcacttgtc gggcaagtca ggacattggt agtagcttaa actggcttca gcaggaacca     180

gatggaacta ttaaacgcct gatctacgcc acatccagtt tagattctgg tgtccccaaa     240

aggttcagtg gcagtaggtc tgggtcagat tattctctca ccatcagcag ccttgagtct     300

gaagattttg tagactatta ctgtctacaa tatgctagtt ctccgtacac gttcggaggg     360

gggaccaagc tggaaataaa acgggctgat gctgcaccaa ctgtatccat cttcccacca     420

tccagtgagc agttaacatc tggaggtgcc tcagtcgtgt gcttcttgaa caacttctac     480

cccaaagaca tcaatgtcaa gtggaagatt gatggcagtg aacgacaaaa tggcgtcctg     540

aacagttgga ctgatcagga cagcaaagac agcacctaca gcatgagcag caccctcacg     600

ttgaccaag                                                             609


<210> SEQ ID NO 13
<211> LENGTH: 1530
<212> TYPE: DNA
<213> ORGANISM: ARTIFICIAL SEQUENCE
<220> FEATURE:
<223> OTHER INFORMATION: SCFV BASED ON MURINE

<400> SEQUENCE: 13

gatcaccggc gaaggagggc caccatggac cccaagggca gcctgagctg gagaatcctg      60

ctgttcctga gcctggcctt cgagctgagc tacggcgagg tgcagcttgt tgagtctggt     120

ggaggattgg tgcagcctaa aggatcattg aaactctcat gtgccgcctc tggtttcacc     180

ttcaatacct atgccatgca ctgggtccgc caggctccag gaaagggttt ggaatgggtt     240

gctcgcataa gaagtaaaag tagtaattat gcaacatatt atgccgattc agtgaaagac     300

agattcacca tctccagaga tgattcacaa agcatgctct atctgcaaat gaacaacctg     360

aaaactgagg acacagccat gtattactgt gtgagagata gaactgggtc ctggtttgct     420

tactggggcc aagggactct ggtcactgtc tctgcaggag gtggcggatc aggtggcgga     480

ggttctggcg gtggcggttc tgacatccag atgacccagt ctccatcctc cttatctgcc     540

tctctgggag aaagagtcag tctcacttgt cgggcaagtc aggacattgg tagtagctta     600
```

```
aactggcttc agcaggaacc agatggaact attaaacgcc tgatctacgc cacatccagt     660

ttagattctg gtgtccccaa aggttcagt  ggcagtaggt ctgggtcaga ttattctctc     720

accatcagca gccttgagtc tgaagatttt gtagactatt actgtctaca atatgctagt     780

tctccgtaca cgttcggagg ggggaccaag ctggaaataa aagacaagac ccacacctgc     840

cctccctgcc ccgcccccga gctgctgggc ggacccagcg tgttcctgtt ccctcccaag     900

cccaaggaca ccctgatgat cagccgcacc cccgaggtga cctgcgtggt ggtggacgtg     960

agccacgagg accccgaggt gaagttcaac tggtacgtgg acggcgtgga ggtgcacaac    1020

gccaagacca agcctcggga ggagcagtac aactccacct accgcgtggt gagcgtgctg    1080

accgtgctgc accaggactg gctgaacggc aaggagtaca agtgcaaggt gagcaacaag    1140

gccctgcccg ctcccatcga gaagaccatc agcaaggcca agggccagcc ccgggagcct    1200

caggtgtaca ccctgccccc cagccgcgac gagctgacca agaaccaggt gagcctgacc    1260

tgcctggtga agggcttcta cccctccgac atcgccgtgg agtgggagag caacggccag    1320

cctgagaaca actacaagac cacccctccc gtgctggaca gcgatggcag cttcttcctg    1380

tacagcaagc tgaccgtgga caagtcccgg tggcagcagg gcaacgtgtt cagctgcagc    1440

gtgatgcacg aggccctgca caaccactac acccagaaga gcctgagcct gagccccgga    1500

tagtgatccc agtgtcccta gctggccaga                                     1530


<210> SEQ ID NO 14
<211> LENGTH: 1530
<212> TYPE: DNA
<213> ORGANISM: ARTIFICIAL SEQUENCE
<220> FEATURE:
<223> OTHER INFORMATION: SCFV BASED ON MURINE

<400> SEQUENCE: 14

gatcaccggc gaaggagggc caccatggac cccaagggca gcctgagctg gagaatcctg      60

ctgttcctga gcctggcctt cgagctgagc tacggcgaca tccagatgac ccagtctcca     120

tcctccttat ctgcctctct gggagaaaga gtcagtctca cttgtcgggc aagtcaggac     180

attggtagta gcttaaactg gcttcagcag gaaccagatg gaactattaa acgcctgatc     240

tacgccacat ccagtttaga ttctggtgtc cccaaaaggt tcagtggcag taggtctggg     300

tcagattatt ctctcaccat cagcagcctt gagtctgaag attttgtaga ctattactgt     360

ctacaatatg ctagttctcc gtacacgttc ggagggggga ccaagctgga aataaaagga     420

ggtggcggat caggtggcgg aggttctggc ggtggcggtt ctgaggtgca gcttgttgag     480

tctggtggag gattggtgca gcctaaagga tcattgaaac tctcatgtgc cgcctctggt     540

ttcaccttca atacctatgc catgcactgg gtccgccagg ctccaggaaa gggtttggaa     600

tgggttgctc gcataagaag taaaagtagt aattatgcaa catattatgc cgattcagtg     660

aaagacagat tcaccatctc cagagatgat tcacaaagca tgctctatct gcaaatgaac     720

aacctgaaaa ctgaggacac agccatgtat tactgtgtga gagatagaac tgggtcctgg     780

tttgcttact ggggccaagg gactctggtc actgtctctg cagacaagac ccacacctgc     840

cctccctgcc ccgcccccga gctgctgggc ggacccagcg tgttcctgtt ccctcccaag     900

cccaaggaca ccctgatgat cagccgcacc cccgaggtga cctgcgtggt ggtggacgtg     960

agccacgagg accccgaggt gaagttcaac tggtacgtgg acggcgtgga ggtgcacaac    1020

gccaagacca agcctcggga ggagcagtac aactccacct accgcgtggt gagcgtgctg    1080

accgtgctgc accaggactg gctgaacggc aaggagtaca agtgcaaggt gagcaacaag    1140
```

```
gccctgcccg ctcccatcga gaagaccatc agcaaggcca agggccagcc ccgggagcct   1200

caggtgtaca ccctgccccc cagccgcgac gagctgacca agaaccaggt gagcctgacc   1260

tgcctggtga agggcttcta ccccctccgac atcgccgtgg agtgggagag caacggccag   1320

cctgagaaca actacaagac cacccctccc gtgctggaca gcgatggcag cttcttcctg   1380

tacagcaagc tgaccgtgga caagtcccgg tggcagcagg gcaacgtgtt cagctgcagc   1440

gtgatgcacg aggccctgca caaccactac acccagaaga gcctgagcct gagccccgga   1500

tagtgatccc agtgtcccta gctggccaga                                   1530


<210> SEQ ID NO 15
<211> LENGTH: 1545
<212> TYPE: DNA
<213> ORGANISM: ARTIFICIAL SEQUENCE
<220> FEATURE:
<223> OTHER INFORMATION: SCFV BASED ON MURINE

<400> SEQUENCE: 15

gatcaccggc gaaggagggc caccatggac cccaagggca gcctgagctg gagaatcctg     60

ctgttcctga gcctggcctt cgagctgagc tacggcgagg tgcagcttgt tgagtctggt    120

ggaggattgg tgcagcctaa aggatcattg aaactctcat gtgccgcctc tggtttcacc    180

ttcaatacct atgccatgca ctgggtccgc caggctccag gaaagggttt ggaatgggtt    240

gctcgcataa gaagtaaaag tagtaattat gcaacatatt atgccgattc agtgaaagac    300

agattcacca tctccagaga tgattcacaa agcatgctct atctgcaaat gaacaacctg    360

aaaactgagg acacagccat gtattactgt gtgagagata gaactgggtc ctggtttgct    420

tactggggcc aagggactct ggtcactgtc tctgcaggct ctacaggagg tggcggatca    480

ggtaaacctg gttctggcga aggaggtggc ggttcagaca tccagatgac ccagtctcca    540

tcctccttat ctgcctctct gggagaaaga gtcagtctca cttgtcgggc aagtcaggac    600

attggtagta gcttaaactg gcttcagcag gaaccagatg gaactattaa acgcctgatc    660

tacgccacat ccagtttaga ttctggtgtc cccaaaaggt tcagtggcag taggtctggg    720

tcagattatt ctctcaccat cagcagcctt gagtctgaag attttgtaga ctattactgt    780

ctacaatatg ctagttctcc gtacacgttc ggagggggga ccaagctgga aataaaagac    840

aagacccaca cctgccctcc ctgccccgcc cccgagctgc tgggcggacc cagcgtgttc    900

ctgttccctc ccaagcccaa ggacaccctg atgatcagcc gcacccccga ggtgacctgc    960

gtggtggtgg acgtgagcca cgaggacccc gaggtgaagt tcaactggta cgtggacggc   1020

gtggaggtgc acaacgccaa gaccaagcct cgggaggagc agtacaactc cacctaccgc   1080

gtggtgagcg tgctgaccgt gctgcaccag gactggctga acggcaagga gtacaagtgc   1140

aaggtgagca acaaggccct gcccgctccc atcgagaaga ccatcagcaa ggccaagggc   1200

cagccccggg agcctcaggt gtacaccctg ccccccagcc gcgacgagct gaccaagaac   1260

caggtgagcc tgacctgcct ggtgaagggc ttctacccct ccgacatcgc cgtggagtgg   1320

gagagcaacg gccagcctga gaacaactac aagaccaccc ctcccgtgct ggacagcgat   1380

ggcagcttct tcctgtacag caagctgacc gtggacaagt cccggtggca gcagggcaac   1440

gtgttcagct gcagcgtgat gcacgaggcc ctgcacaacc actacaccca gaagagcctg   1500

agcctgagcc ccggatagtg atcccagtgt ccctagctgg ccaga                   1545


<210> SEQ ID NO 16
```

<211> LENGTH: 1545
<212> TYPE: DNA
<213> ORGANISM: ARTIFICIAL SEQUENCE
<220> FEATURE:
<223> OTHER INFORMATION: SCFV BASED ON MURINE

<400> SEQUENCE: 16
gatcaccggc gaaggagggc caccatggac cccaagggca gcctgagctg gagaatcctg 60
ctgttcctga gcctggcctt cgagctgagc tacggcgaca tccagatgac ccagtctcca 120
tcctccttat ctgcctctct gggagaaaga gtcagtctca cttgtcgggc aagtcaggac 180
attggtagta gcttaaactg gcttcagcag gaaccagatg gaactattaa acgcctgatc 240
tacgccacat ccagtttaga ttctggtgtc cccaaaaggt tcagtggcag taggtctggg 300
tcagattatt ctctcaccat cagcagcctt gagtctgaag attttgtaga ctattactgt 360
ctacaatatg ctagttctcc gtacacgttc ggaggggga ccaagctgga aataaaaggc 420
tctacaggag gtggcggatc aggtaaacct ggttctggcg aaggaggtgg cggttcagag 480
gtgcagcttg ttgagtctgg tggaggattg gtgcagccta aaggatcatt gaaactctca 540
tgtgccgcct ctggtttcac cttcaatacc tatgccatgc actgggtccg ccaggctcca 600
ggaaagggtt tggaatgggt tgctcgcata agaagtaaaa gtagtaatta tgcaacatat 660
tatgccgatt cagtgaaaga cagattcacc atctccagag atgattcaca aagcatgctc 720
tatctgcaaa tgaacaacct gaaaactgag gacacagcca tgtattactg tgtgagagat 780
agaactgggt cctggtttgc ttactggggc caagggactc tggtcactgt ctctgcagac 840
aagacccaca cctgccctcc ctgccccgcc cccgagctgc tgggcggacc cagcgtgttc 900
ctgttccctc ccaagcccaa ggacaccctg atgatcagcc gcacccccga ggtgacctgc 960
gtggtggtgg acgtgagcca cgaggacccc gaggtgaagt tcaactggta cgtggacggc 1020
gtggaggtgc acaacgccaa gaccaagcct cgggaggagc agtacaactc cacctaccgc 1080
gtggtgagcg tgctgaccgt gctgcaccag gactggctga acggcaagga gtacaagtgc 1140
aaggtgagca acaaggccct gcccgctccc atcgagaaga ccatcagcaa ggccaagggc 1200
cagccccggg agcctcaggt gtacaccctg ccccccagcc gcgacgagct gaccaagaac 1260
caggtgagcc tgacctgcct ggtgaagggc ttctacccct ccgacatcgc cgtggagtgg 1320
gagagcaacg gccagcctga gaacaactac aagaccaccc ctcccgtgct ggacagcgat 1380
ggcagcttct tcctgtacag caagctgacc gtggacaagt cccggtggca gcagggcaac 1440
gtgttcagct gcagcgtgat gcacgaggcc ctgcacaacc actacaccca gaagagcctg 1500
agcctgagcc ccggatagtg atcccagtgt ccctagctgg ccaga 1545

<210> SEQ ID NO 17
<211> LENGTH: 120
<212> TYPE: PRT
<213> ORGANISM: MURINE SP.

<400> SEQUENCE: 17

Glu Val Gln Leu Val Glu Ser Gly Gly Gly Leu Val Gln Pro Lys Gly
1 5 10 15

Ser Leu Lys Leu Ser Cys Ala Ala Ser Gly Phe Thr Phe Asn Thr Tyr
20 25 30

Ala Met His Trp Val Arg Gln Ala Pro Gly Lys Gly Leu Glu Trp Val
35 40 45

Ala Arg Ile Arg Ser Lys Ser Ser Asn Tyr Ala Thr Tyr Tyr Ala Asp
50 55 60

-continued

```
Ser Val Lys Asp Arg Phe Thr Ile Ser Arg Asp Asp Ser Gln Ser Met
65                  70                  75                  80

Leu Tyr Leu Gln Met Asn Asn Leu Lys Thr Glu Asp Thr Ala Met Tyr
                85                  90                  95

Tyr Cys Val Arg Asp Arg Thr Gly Ser Trp Phe Ala Tyr Trp Gly Gln
            100                 105                 110

Gly Thr Leu Val Thr Val Ser Ala
        115                 120


<210> SEQ ID NO 18
<211> LENGTH: 107
<212> TYPE: PRT
<213> ORGANISM: MURINE SP.

<400> SEQUENCE: 18

Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Asp Ile Gly Ser Ser
            20                  25                  30

Leu Asn Trp Leu Gln Gln Glu Pro Asp Gly Thr Ile Lys Arg Leu Ile
        35                  40                  45

Tyr Ala Thr Ser Ser Leu Asp Ser Gly Val Pro Lys Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Phe Val Asp Tyr Tyr Cys Leu Gln Tyr Ala Ser Ser Pro Tyr
                85                  90                  95

Thr Phe Gly Gly Gly Thr Lys Leu Glu Ile Lys
            100                 105
```